United States Patent [19]
Lander

[11] Patent Number: 5,656,904
[45] Date of Patent: Aug. 12, 1997

[54] MOVEMENT MONITORING AND CONTROL APPARATUS FOR BODY MEMBERS

[76] Inventor: Ralph Lander, 1 W. 85th St. Apt. 3D, New York, N.Y. 10025

[21] Appl. No.: 535,621

[22] Filed: Sep. 28, 1995

[51] Int. Cl.⁶ .................. B25J 9/08; B25J 15/08
[52] U.S. Cl. .................. 318/568.12; 318/568.1; 318/568.18; 414/680; 414/730; 901/21; 901/23
[58] Field of Search .................. 318/560–696; 294/111; 623/24, 25, 57, 63, 64, 66; 74/479.01, 479.02, 417, 423, 469; 901/15, 21, 12, 23, 25, 17, 20, 26, 28, 19, 36, 38, 29, 39; 414/4, 5, 378, 680, 729, 730, 732, 735, 737, 744.5; 464/109

[56] References Cited

U.S. PATENT DOCUMENTS

| | | | |
|---|---|---|---|
| 4,246,661 | 1/1981 | Pinson | 3/1.1 |
| 4,302,138 | 11/1981 | Zarudiansky | 414/5 |
| 4,566,843 | 1/1986 | Iwatsuka et al. | 414/680 |
| 4,568,311 | 2/1986 | Miyake | 464/109 |
| 4,575,297 | 3/1986 | Richter | 414/5 |
| 4,600,355 | 7/1986 | Johnson | 414/680 |
| 4,662,814 | 5/1987 | Suzuki et al. | 414/730 |
| 4,697,472 | 10/1987 | Hiyane | 74/479 |
| 4,766,775 | 8/1988 | Hodge | 74/479 |
| 4,828,453 | 5/1989 | Martin et al. | 414/738 |
| 4,865,376 | 9/1989 | Leaver et al. | 294/111 |
| 4,868,549 | 9/1989 | Affinito et al. | 340/710 |
| 4,921,293 | 5/1990 | Ruoff et al. | 294/111 |
| 4,946,380 | 8/1990 | Lee | |
| 4,955,918 | 9/1990 | Lee | 623/24 |
| 4,986,280 | 1/1991 | Marcus et al. | 128/774 |
| 4,988,981 | 1/1991 | Zimmerman et al. | 340/709 |
| 5,049,797 | 9/1991 | Phillips | 318/568.16 |
| 5,062,673 | 11/1991 | Mimura | 294/111 |
| 5,080,682 | 1/1992 | Schectman | 623/64 |
| 5,092,646 | 3/1992 | Smallridge | 294/111 |
| 5,143,505 | 9/1992 | Burdea et al. | 414/5 |
| 5,166,462 | 11/1992 | Suzuki et al. | 84/600 |
| 5,195,388 | 3/1993 | Zona et al. | 74/479 |
| 5,280,265 | 1/1994 | Kramer et al. | 338/210 |
| 5,447,403 | 9/1995 | Engler, Jr. | 414/4 |
| 5,523,662 | 6/1996 | Goldenberg et al. | 318/568.11 |

*Primary Examiner*—Paul Ip
*Attorney, Agent, or Firm*—Watov & Kipnes, P.C.

[57] ABSTRACT

Basic interchangeable building blocks such as to create a structure and/or an exoskeleton for an apparatus for monitoring and controlling the movements of body members comprising a single axis joint adaptable axis joint, an axial rotation joint, a wrist rotation joint and a linear motion transmission joint, all of which can be spring controlled and/or be controlled by a rotation transmitting cable each having means for producing electrical signals indicative of their movement and can be coupled together so as to permit electrical conduction and rotation transmitting cables to be passed through them.

6 Claims, 19 Drawing Sheets

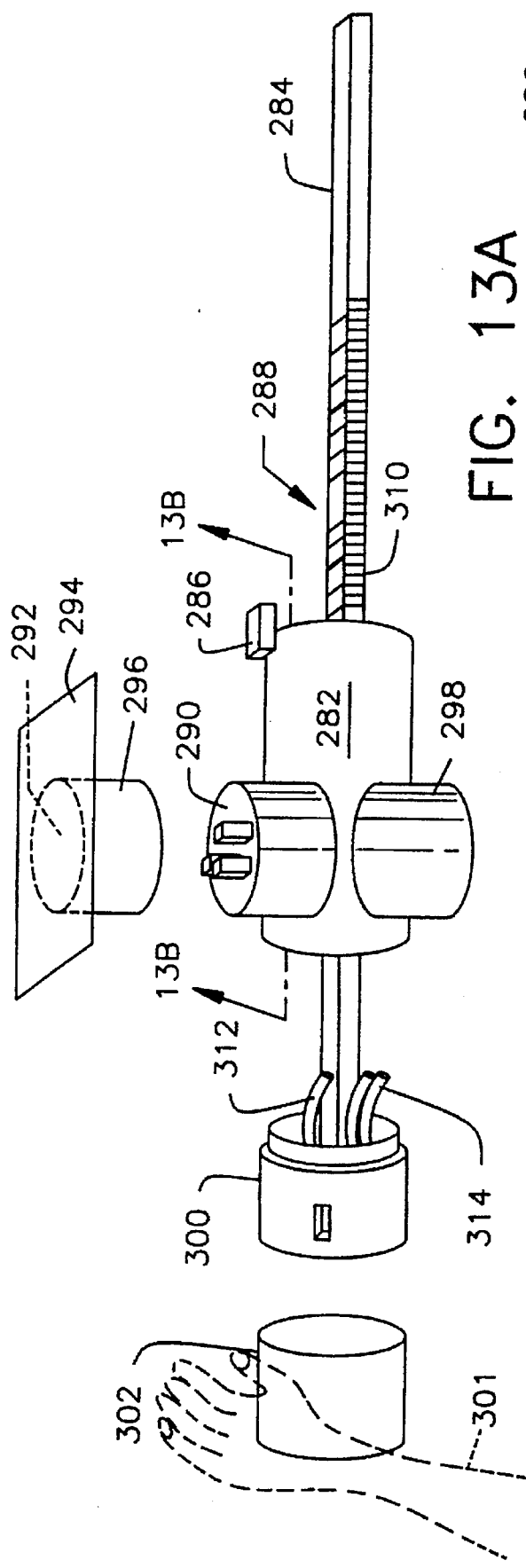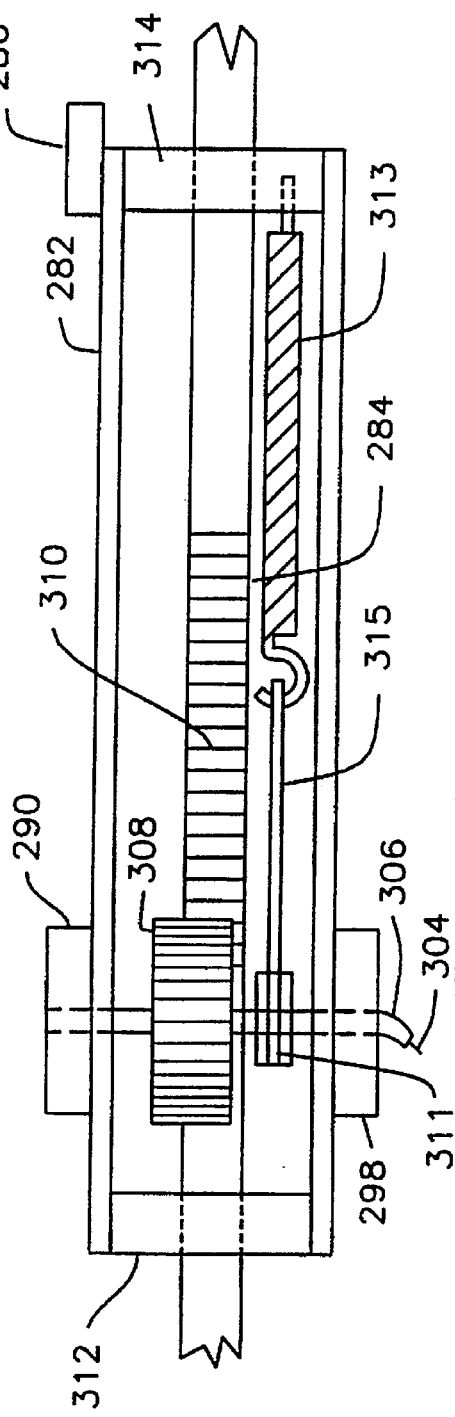

MOVEMENT MONITORING AND CONTROL APPARATUS FOR BODY MEMBERS

FIELD OF THE INVENTION

This invention is in the field of robotic devices for monitoring and controlling the movement of human limbs and body joints, and mechanical members.

BACKGROUND OF THE INVENTION

Over the past 50 years, the technology associated with robotic apparatus has grown dramatically. In the early 1940's, the field of technology for robotic apparatus was significantly advanced during the development of atomic weapons. At that time, it was necessary to develop robotic tools, such as robotic hands that could be operated remotely, a safe distance from radioactive substances being transferred from one vessel to another, for example. With the development of nuclear reactors for peace time uses, such as for providing electrical power, new robotic devices were developed for permitting an operator to remotely disassemble radioactive fuel assemblies, or to repair such fuel assemblies, or even reload the assemblies with new fuel, while the assemblies are under water. As robotic apparatus or devices progressed in development, it became apparent that apparatus for both monitoring the movement of mechanical members and controlling the movement thereof, are of great importance in furthering the robotic technology.

Today, the field of robotics is used in many different applications. For example, robotic devices are used in the medical field, for use in physical therapy apparatus, such as exercise machines, and so forth. Robotics also are used extensively in the entertainment industry, for applications ranging from unusual visual effects for movies, to apparatus associated with virtual reality systems.

It has become increasingly apparent that improvements must be made in apparatus for precisely monitoring the movement of human limbs, or mechanical members of machines or other apparatus, in order to improve tracking and feedback mechanisms associated therewith. Also, it has become increasingly apparent that robotic mechanisms must be further developed for providing improved control, tactile feedback, and force delivery mechanisms responsive to signals from movement monitoring subsystems of integrated robotic systems. The present inventor recognized the need for improved robotic devices in association with the monitoring of the movement of various limbs of a human body, and with the analogous monitoring of mechanical members. The present inventor also recognized the need for improved systems for imparting movement to human limbs and other mechanical members, and for monitoring such movement.

In medical therapy apparatus, it may be important to exercise a certain limb. To accomplish a certain exercising routine for a limb, it is equally important to know how far a limb has moved, as it is to know the amount of force being applied to the limb at any given time for causing movement in a certain direction. Through the use of precise monitoring of movement of the limb, and appropriate force feedback, very accurate routines for both exercising a given limb and measuring the progress of a given therapy routine, can be obtained. In virtual reality systems it is important to know how a user has moved their limbs in response to certain stimuli, in order to feedback appropriate images, stimulus, and perhaps forced movement of limbs, in response to signals associated with the monitored activity of the users body. Accordingly, there is a continuous need for improved apparatus and devices for monitoring the movement of human and mechanical members, and controlling such movement.

Robotic devices are known for moving an artificial hand in accordance with the movement of a person's hand and for monitoring the rotations of the various joints of the artificial hand. It is also known to attach an artificial hand to a person's hand so as to control and/or monitor the rotation of the joints thereof.

Among the disadvantages of prior apparatus are that it is cumbersome so as to inhibit the motion of a person's hand when attached thereto, the communication between a controller and the joint is rather inflexible and easy attachment/ detachment of such apparatus is rather difficult if not impossible. Furthermore, prior apparatus components are not adaptable to the user "hand" size or "finger" length.

SUMMARY OF THE INVENTION

In accordance with this invention for monitoring and controlling movement of human limbs, and mechanical members, one axis, two axis, axial rotation and linear following joints are provided that are moved in response to the rotation of rotation transmission cables, and the actual movement of the joints is monitored by absolute or relative optical encoders that provide electrical signals indicative of that movement. Male and female connectors are provided at opposite ends of the joints so that they can be snapped together, as, for example, where successive joints are respectively used to monitor or control the rotation of the wrist and the joints of the fingers, for example.

The connectors are such that the rotation of a rotation transmission cable coupled to them can be communicated to a similar cable in the other. Thus the rotation transmission cable for operating a joint can be coupled to a connector and the rotation of cables from another joint can be passed through the joint between its male and female connectors. Provision is also made for conductors carrying rotation monitoring signals of a joint to pass through its male or female connector or to exit from the joint. Conductors from other joints can pass through another. These coupling structures make it possible to obtain great flexibility in operating and monitoring the rotation of the joints of a system such as a system associates with a hand.

In order to facilitate coupling one joint to another, springs are provided for making the rotation transmission members in the male and female joints have the same orientation so that a rectangular end of a member in a male connector can be easily inserted into a like shaped cavity in a member of the female connector.

In accordance with a feature of the invention, a joint is provided that can operate and monitor the rotation of a human wrist about an axis extending through the elbow. A flexible band is provided that is secured at its ends to the outer bones of a wrist and which runs between a plurality of parallel rollers that are mounted on the upper arm so as to be independent of the wrist rotation. A rotation transmission cable is coaxially connected to one of the rollers so that the wrist can be rotated, and the amount of rotation is monitored by an encoder.

The invention also includes means for restoring the joints to a preset position when no forces are applied to them. Another feature of the invention is a means for remotely opening and closing clamps for holding joints on the fingers so as to make it easier to mount a combination of joints on a hand. In addition longitudinal spring action can be provided in the coupling of one joint to another so as to achieve a good fit to a user's hand.

BRIEF DESCRIPTION OF THE DRAWINGS

Various embodiments of the present invention are described below with reference to the drawings, in which like items are identified by the same reference designation, and in which:

FIGS. 12A and 2B illustrate a joint for controlling and monitoring the rotation of a wrist about an axis through the elbow;

FIGS. 13A and 13B illustrate a linear motion mechanism;

DETAILED DESCRIPTION OF THE INVENTION

Figure 1:
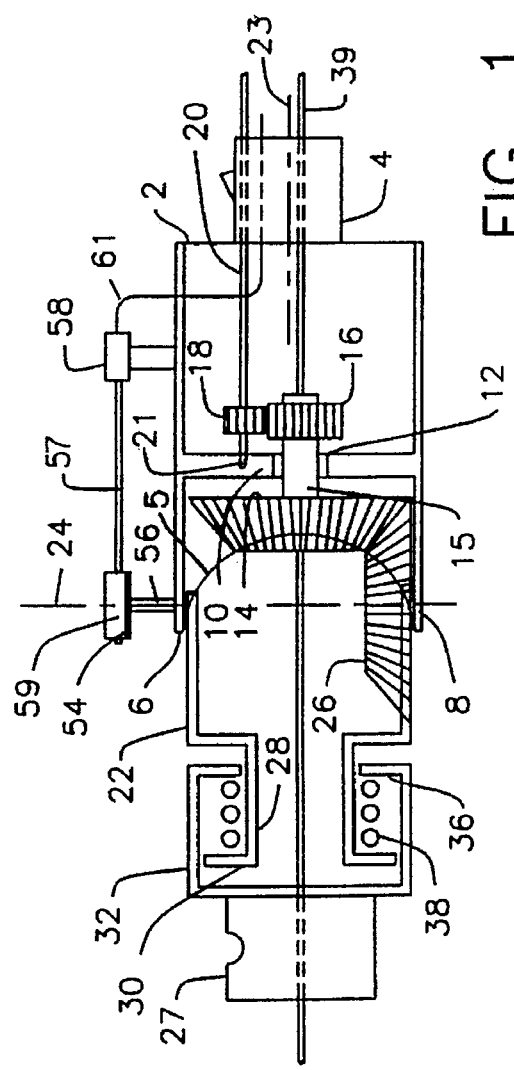
FIG. 1 is a sectional view of a one axis joint.

FIG. 1 is drawn as though the components are made of transparent material. In the single axis joint shown therein, a first cylinder 2 is shown as having a male connector 4 attached at one end that will be described in detail below. U or oval shaped notches such as the notch 5 are formed in opposite sides at the other end of the cylinder 2 so as to form points 6 and 8. An annular wall 10 that is attached to the cylinder 2 extends inwardly from an intermediate point in the cylinder 12, and a bearing such as a race 12 is secured to its inner surface. A beveled toothed gear 14 is attached to one end of an hollow axle 15 that is mounted for rotation in the bearing race 12, and an annular gear 16 is mounted about the other end of the hollow axle 15. A smaller gear 18 that meshes with the gear 16 is mounted on the end of a cable 20 that transmits rotation so that the cable 20, the gear 18, the gear 16, the axle 15 and the gear 14 rotate together. In order to provide stability, the inner end 21 of the cable 20 is mounted for rotation in the annular wall 10. Alternatively, the beveled gear 14 could be mounted at one end of a hub 324 shown in FIG. 14A that is rotated as described in connection therewith.

Another cylinder 22 is mounted within the cylinder 2 so that its axis can coincide with the axis 23 of the cylinder 2 and so that it can pivot about an axis 24 extending through the points 6 and 8. A beveled gear 26 is mounted on the inside of the cylinder 22 with its axis coinciding with the axis 24 and with its toothed periphery meshing with the teeth on the gear 14. Thus, when the cable 20 is rotated, the gear 26 rotates about the axis 24 and carries the cylinder 22 with it.

In order to permit transational movement between the male connector 4 and a female connector 27 at the other end of the joint in accordance with an aspect of this invention, a cylinder 28 of smaller diameter than the cylinder 22 is mounted coaxially therewith so as to protrude from the end of the cylinder 22 that is remote from the cylinder 2. An annular flange 30 at the end of the cylinder 28 that is nearer the female connector 27 is provided. A fourth cylinder 32 has the female connector 27 that will be described below affixed at one end and an inwardly extending annular flange 36 at the other. The flange 30 is in sliding contact with the cylinder 32, and the flange 36 is in sliding contact with the cylinder 28. A coiled compression spring 38 is mounted between the flange 30 and the flange 36. Thus, any tension between the male connector 4 and the female connector 27 will squeeze the spring 38, and the assembly will resume its original position when the tension is released.

One of the advantages of the joints of this invention is that rotation translating cables and electrical signal conductors that may carry signals indicative of the rotational position of a joint can be passed through them, eg a cable 39 passes through the connector 4, the cylinder 2, the annular gear 16, the hollow axle 15, cylinders 22, 28 and 32 and the connector 27. Conductors carrying position monitoring signals can follow the same path.

Figure 2B:
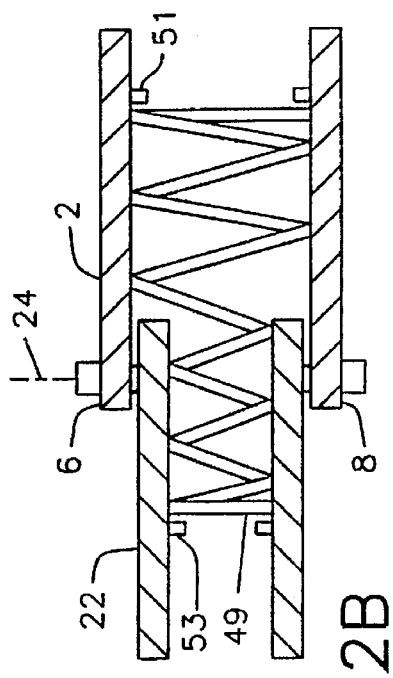
FIG. 2B illustrates another mechanism for restoring a single axis joint to a preset position.
Figure 2A:
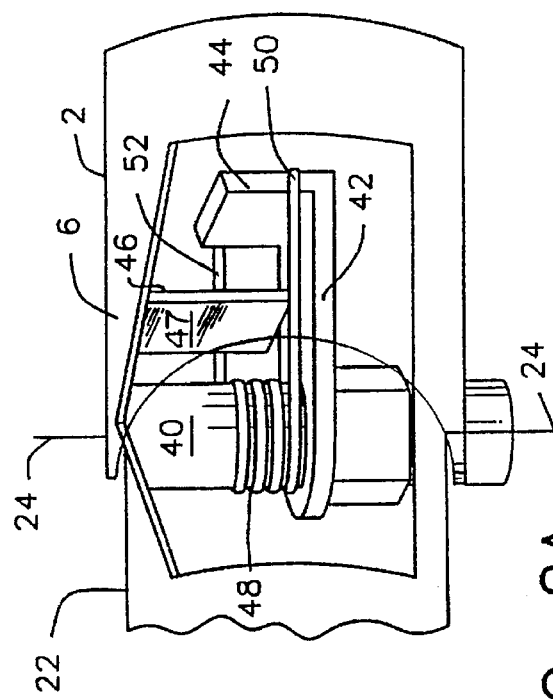
FIG. 2A is an enlarged view of a mechanism for restoring the single axis joint of FIG. 1 to a preset position.

If it is desired to return the cylinder 2 and the cylinder 22 into axial alignment after they have been positioned out of such alignment by forces applied directly to them or by rotation of the cable 20, a mechanism such as shown in FIG. 2A can be used. A rod 40 is mounted in the cylinder 22 so as to be aligned with the axis 24 and turn with the cylinder 22. One end of a radial arm 42 is secured to the rod 40, and its other end 44 is bent at a right angle so as to be parallel to the rod 40. One end of a bar 46 is rigidly attached to the inside of the cylinder 2 so as to have its other end 47 parallel to and spaced from the end 44 of the arm 42. A spring 48 is wound about the rod 40 with its ends 50 and 52 respectively on opposite sides of the bent end 44 of the radial arm 42 and the end 47 of the bar 46. Torque causing relative rotation of the cylinders 2 and 22 about the axis 24 will spread the ends 50 and 52 of the spring 40 apart so that when the torque is released, the cylinders resume axial alignment. This system can be applied to any of the other joint mechanism 1.

Reference is made to FIG. 2B for description of another way of returning the cylinders 2 and 22 into axial alignment after forces have been removed from them. A coiled spring such as a compression spring 49 having the same or less diameter, than the inner diameter of the larger of the cylinders 2 and 22, in this case the cylinder 2, is mounted within the proximate ends of the cylinders and retained in position by annular ridges 51 and 53 within the cylinders 2 and 22 respectively. Although the cylinder 2 is shown as having the larger diameter, the diameter of the cylinder 22 could be larger.

Referring again to FIG. 1, when the angle between the cylinders 2 and 22 is being controlled by rotation of the cable 20, the actual angle could be predicted from the amount that the cable 20 is rotated, but this is not precise. Accordingly, means are provided for monitoring the angle. One way of doing this is to firmly mount a disc 54 by means of an pin 56 in the axis 24 that extends through a hole in the cylinder 2, not shown, to the cylinder 22 so that the disc 54 rotates with the cylinder 22 about the axis 24. One end of a fibre optic element 57 is inserted into a hollow pipe 59 that is mounted on the disc 54 in a direction perpendicular to the axis 24 so as to rotate with the disc 54 and permit that end of the optical fibre 57 to slide longitudinally therein. The other end of the fibre optic element 57 is held in a clamp 58 that is affixed to the cylinder 2 at some distance from the axis 24. Light is introduced into the end of the fibre optic element 57 that is remote from the end attached to the disc 54 by means not shown, that is energized by wires in a bundle 61 and a reflecting surface, not shown, is located at the end of the fibre 57 that is nearer to the disc 54. As the angle between the cylinders 2 and 22 changes, the portion of the optical fibre element 57 between the pipe 59 and the clamp 58 is bent as the disc 54 rotates so as to change the amount of reflected light. The amount of light so reflected can be calibrated so as to indicate the desired angle, and a signal indicative of the amount of reflected light is conveyed by wires in the bundle 61.

Figure 3A:
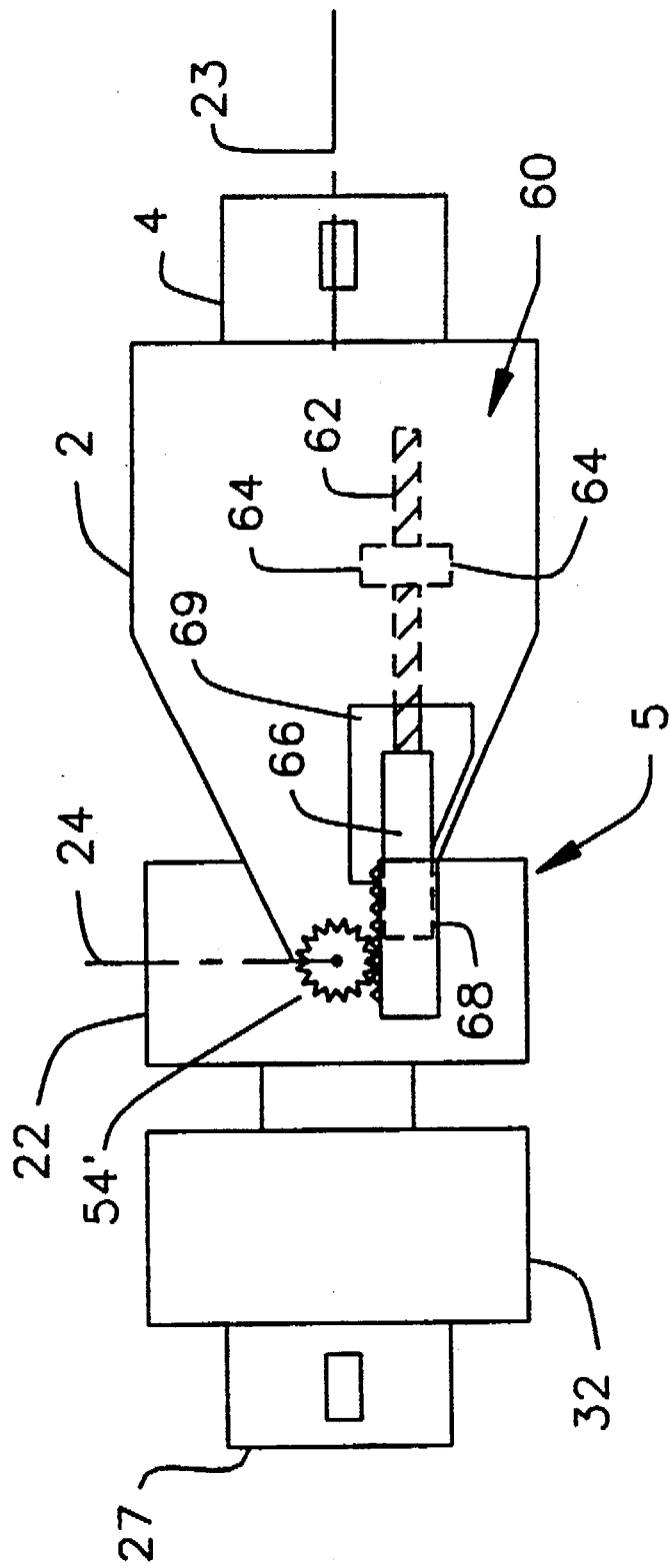
FIGS. 3A and 3B illustrate a specie of a mechanism for monitoring the angle of rotation of a single axis joint part of which is located on the outside of the joint.
Figure 3B:
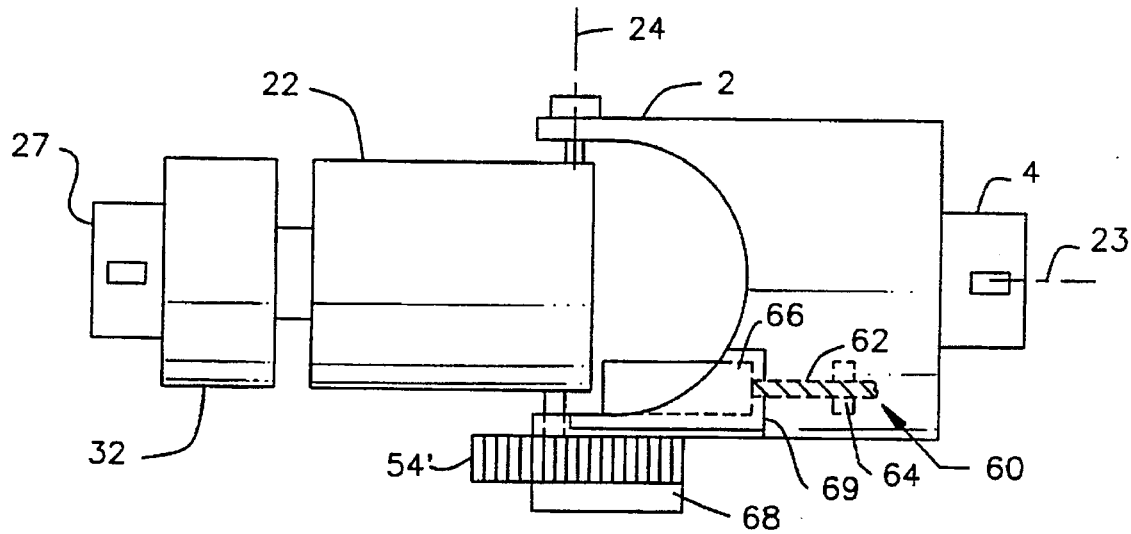

One mechanical way of monitoring the angle between the cylinders 2 and 22 of FIG. 1 is illustrated in FIGS. 3A and 3B. A shaft 60 having a low pitched external thread 62 thereon is mounted for axial rotation on the inside of the cylinder 2 by any suitable means 64 so as to be parallel to the axis 23 of the cylinder 2, and a nut 66 having internal threads that mate with the threads 62 on the shaft 60 is threaded onto the shaft 60. A plate 68 having gear teeth thereon is attached to the nut 66 so as to be parallel to the axis 23 and in contact with the disc 54, and the cylinder 2 is cut away as indicated at 69 so as to permit axial movement of the plate 68. Teeth on the disc 54 mate with the teeth on the plate 68. The disc 54' is like the disc 54 except that it has gear teeth around its periphery. As the angle between the cylinders 2 and 22 changes, the disc 54 rotates with respect to the plate 68 causing it to drive the plate 68 and the nut 66 along the shaft 60 so as to turn the shaft 60. The amount by which the shaft 60 turns indicates the angle between the cylinders 2 and 22.

Figure 3C:
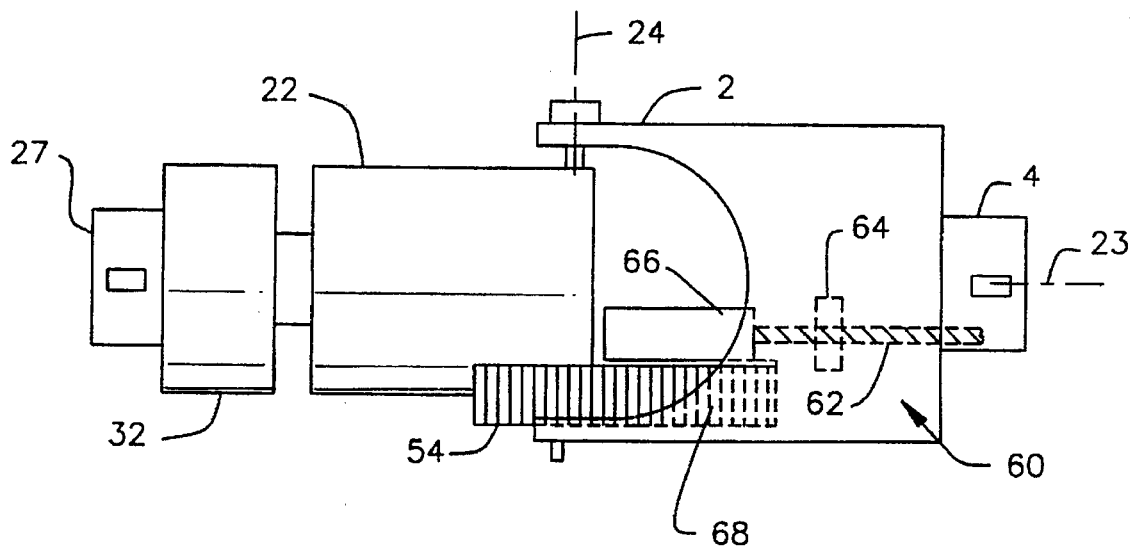
FIG. 3C illustrates a mechanism like that of FIGS. 3A and 3B that is entirely located on the inside of the joint.

FIG. 3C shows a mechanism having the same component parts as shown in FIGS. 3A and 3B, but with the difference that they are mounted within the confines of the cylinder 2.

Figure 4:
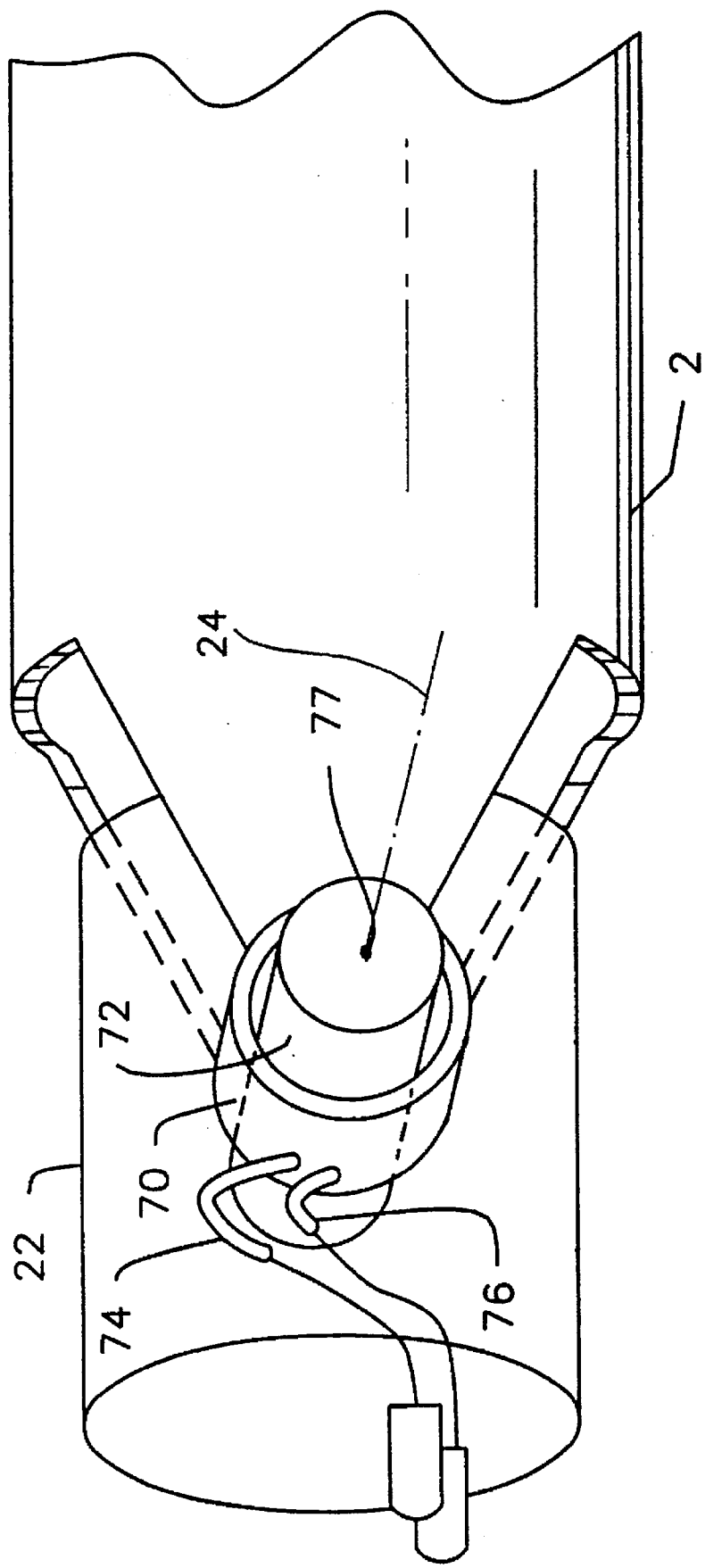
FIG. 4 illustrates a way of monitoring rotation about an axis.

An electronic way of monitoring the angular position of a single joint such as shown in FIG. 1, is illustrated in FIG. 4 wherein a device 70 operates in a known manner to produce an electrical signal on conductors 74 and 76 indicative of the angular position of a shaft 77 that is mounted so as to rotate with the cylinder 22 about the axis 24. This can also be implemented in other joints.

As previously noted, the devices of this invention have male and female connectors such as 4 and 27 of FIG. 1 at opposite ends so that the male connector of one device can be snapped onto the female device of another in such manner that the rotation of a wire of a rotation transmission cable can be transmitted from one device to another or completely through a device as in the case of the cable 39 of FIG. 1.

Figure 5A:
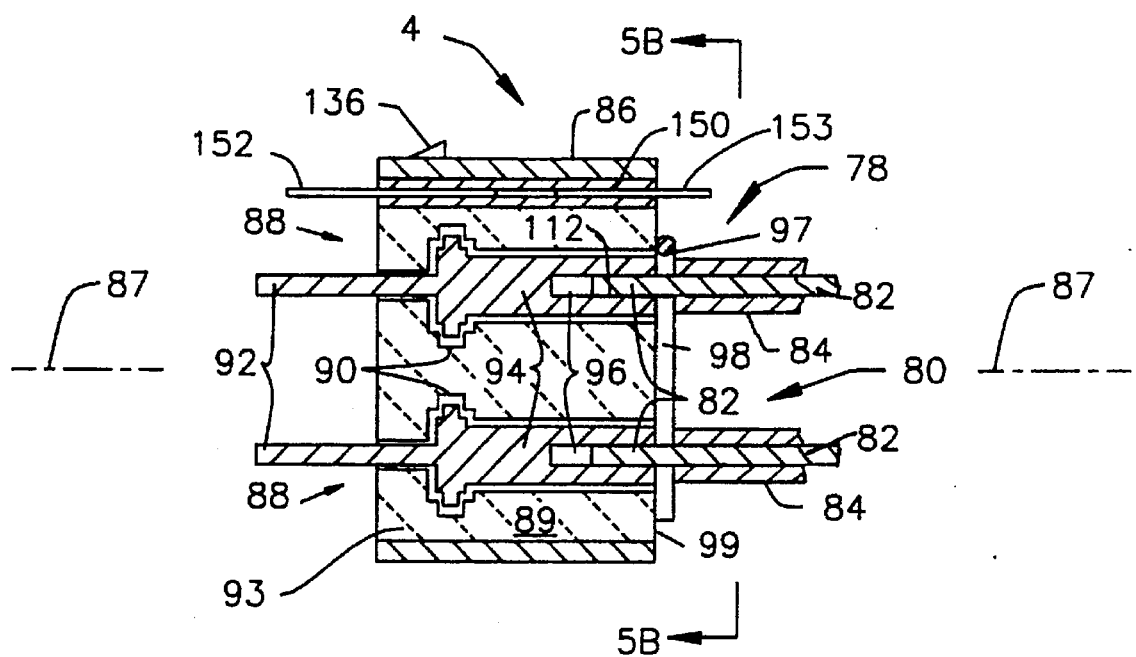
FIGS. 5A and 5B are different cross sectional views of a male connector.

In the cross sectional view of a male connector 4 shown in FIG. 5A, two identical rotation transmitting cables 78 and 80 that come from a device being coupled or which are passed through that device from another are shown. Corresponding parts of the connector 4 for transmitting the rotation of the cables 78 and 80 are designated by the same numbers. The function of the cables 78 and 80 is to transmit rotary motion without becoming snarled by winding around themselves. Although various kinds of rotation transmission cables can be used for this purpose, the particular cables 78 and 80 shown are like speedometer cables used in automobiles in which a flexible wire 82 is contained within a tubular housing 84. For reasons which will be explained, the wire 82 preferably has a circular cross section between ends having rectangular a cross section or any shape other than a circle. The dimensions of the housing 84 and the wire 82 are such that the wire 82 can freely rotate about its axis without becoming snarled. Because of the short distance between male and female connectors of a joint, the housing 84 is not necessary. Other rotation transmitting cables not requiring a housing can be used such as one using links that are connected so as to pivot in one plane at one end and in a perpendicular plane at the other.

The male connector 4 of FIG. 5A is contained within a cylindrical housing 86. In this particular illustration, only two rotation transmitting cables 78 and 80 are shown in order to simplify the drawing, but more could be involved. A longitudinal member 88 is mounted in a potting compound 89 so as to be parallel to the axis 87 of the housing 86 in such manner as to rotate about its own axis. The member 88 is mounted for rotation in an annular bearing 90 that is retained in the potting compound 89. One end of the member 88 is a male prong 92 of a rectangular cross section that extends beyond a wall 93 of the potting compound 89, and the other end of the member 88 is a tube 94. The prong 92 could be three sided or have any cross section other than a circle. A cavity 96 within the tube 94 has a cross section so as to fit the prong of the wire 82 of the rotation transmission cable 78. Thus rotation of the wire 82 causes the member 88 and therefore its prong 92 to rotate, and, similarly, rotation of the prong 92 will cause the wire 92 to rotate.

Figure 5B:
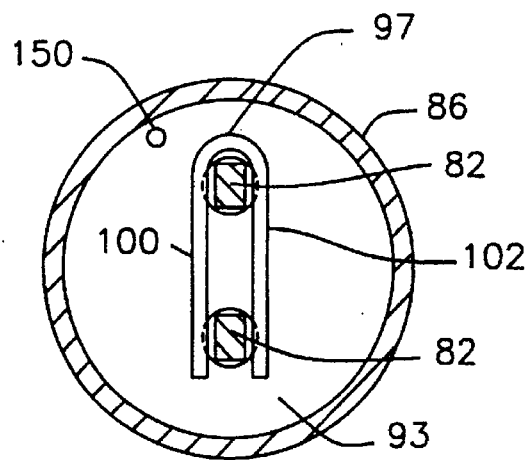

In order that the rectangular prong 92 of the member 88 that extends through the radial wall 93 have a predetermined axial orientation when no torque is applied to it so as make it easy to insert it into similarly oriented cavity in a female connector to be described, the closed end 97 of a U shaped spring 98 is attached to a wall 99 of the potting compound 89 that is parallel to the wall 93 in any suitable manner such that its arms 100 and 102 lie on opposite sides of the rectangular wires 82 of the cables 78 and 80 as shown in FIG. 5B. When torque is applied to a wire 82, it turns and spreads the arms 100 and 102 apart, but when the torque is removed, the arms 100 and 102 turn the wire 82 back to the position shown in FIG. 5B. This causes the prongs 92 of the male connector 4 to resume their initial position. Alternatively, the spring 97 could be placed on the wall 93 so that its arms 100 and 102 straddle the prongs 92.

Figure 6A:
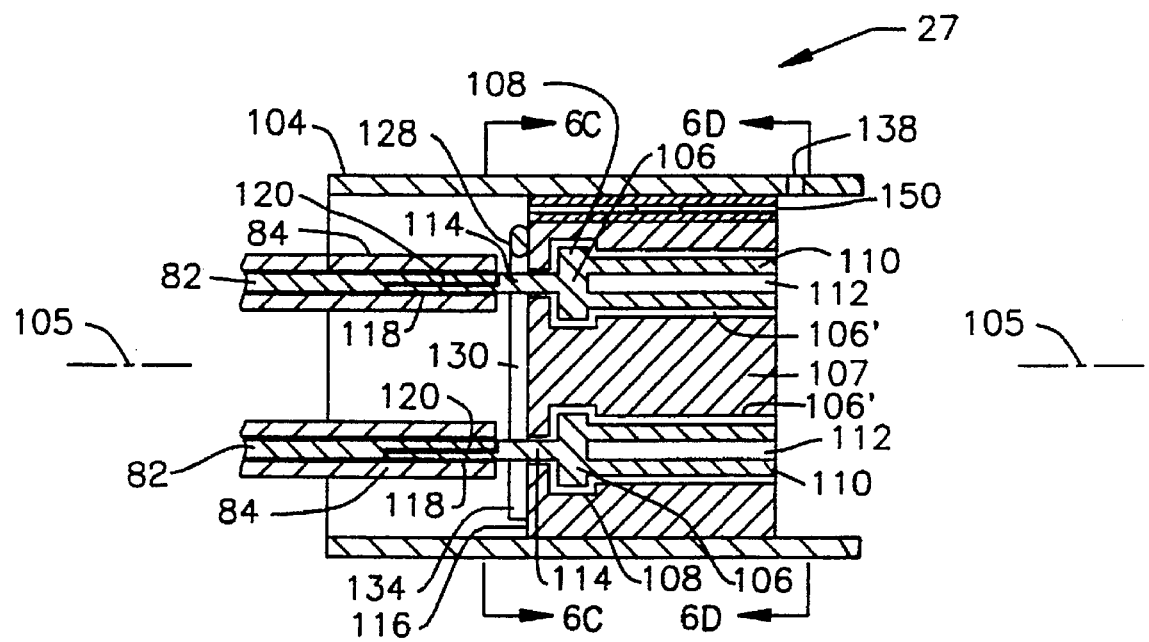
FIGS. 6A, 6B, 6C and 6D are sectional views of one species of female connector.
Figure 6B:
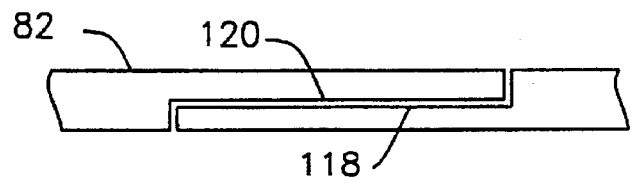
Figure 6C:
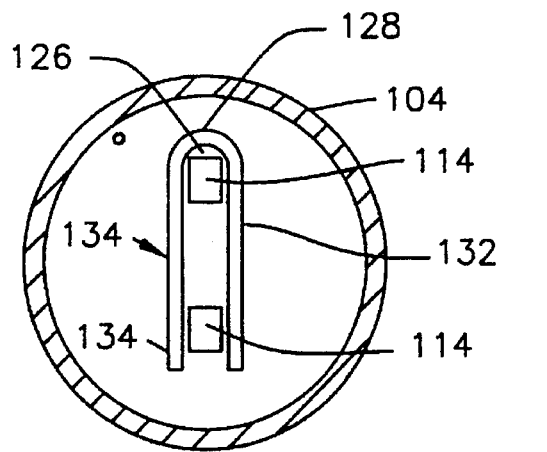

FIGS. 6A, 6B and 6C illustrate a female connector 27 into which the male prongs 92 of the male connector 4 of FIG.

5A may be plugged. Corresponding parts of the two male prong receiving means are similarly designated, but only one will be described.

In the cross section of FIG. 6A, the female connector 27 is shown as being comprised of a housing 104 that in FIGS. 6B and 6C is shown as being cylindrical. A longitudinal member 106 is mounted for axial rotation in a passageway 106' in a potting compound 107 that is parallel to the axis 105 of the cylindrical housing 104. Axial rotation of the member 106 is facilitated by a bearing 108. A tube 110 having an axial cavity 112 therein extends from one side of the member 106. The cavity 112 has a three sided or rectangular cross section or any cross section other than a circle so as to receive a similarly shaped prong 92 of the male connector shown in FIG. 5A. A prong 114 of rectangular cross section extends from the other end of the member 106 and beyond a wall 116 at one end of the potting compound 107. The prong 114 is flattened at 118 as more clearly shown in FIG. 6B to one half its thickness, and an end 120 of a rotation translation wire 82 that is to be connected between male and female connectors of a joint is similarly flattened to one half thickness. The flattened end 118 of the prong 114 and the flattened end 120 of the wire 82 fit alongside each other so that rotation of one causes the other to rotate.

Figure 6D:
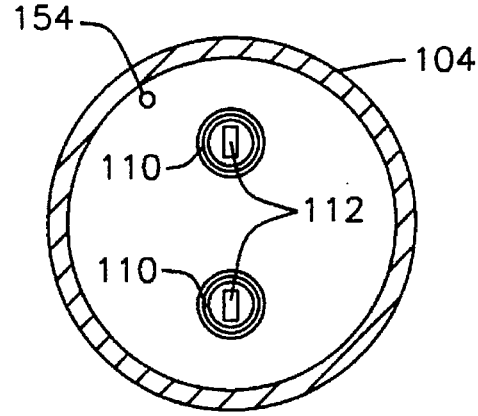

In order that the cylindrical members 106 be in a rest position such that their rectangular cavities 112 will be aligned with rectangular ends 92 of the male connector 4 as shown in FIG. 5B, the closed end 128 of a U shaped spring 130 is attached to the wall 116 so that, as seen in FIG. 6C, which is section 6C, 6C of FIG. 6A, its arms 132 and 134 lie on opposite sides of the prongs 114. The U shaped spring 130 Operates to orient the prongs 114 within it in the same way as was described in connection with the spring 98 of FIGS. 5A and 5B. FIG. 6D is a section 6D, 6D of FIG. 6A showing the ends of the tubes 110 and cavities 112 therein.

The housing cylinder 86 of the male connector of FIG. 5A has an external diameter that is less than the internal diameter of the housing cylinder 104 of the female connector of FIG. 6A so that it can be inserted into the cylinder 104. A releasable latching means is provided for holding them together, as, for example, an outwardly extending tongue 136 on the cylinder 86 of the male connector of FIG. 5A that snaps into an aperture 138 in the cylinder 104 of the female connector of FIG. 6A.

Figure 6E:
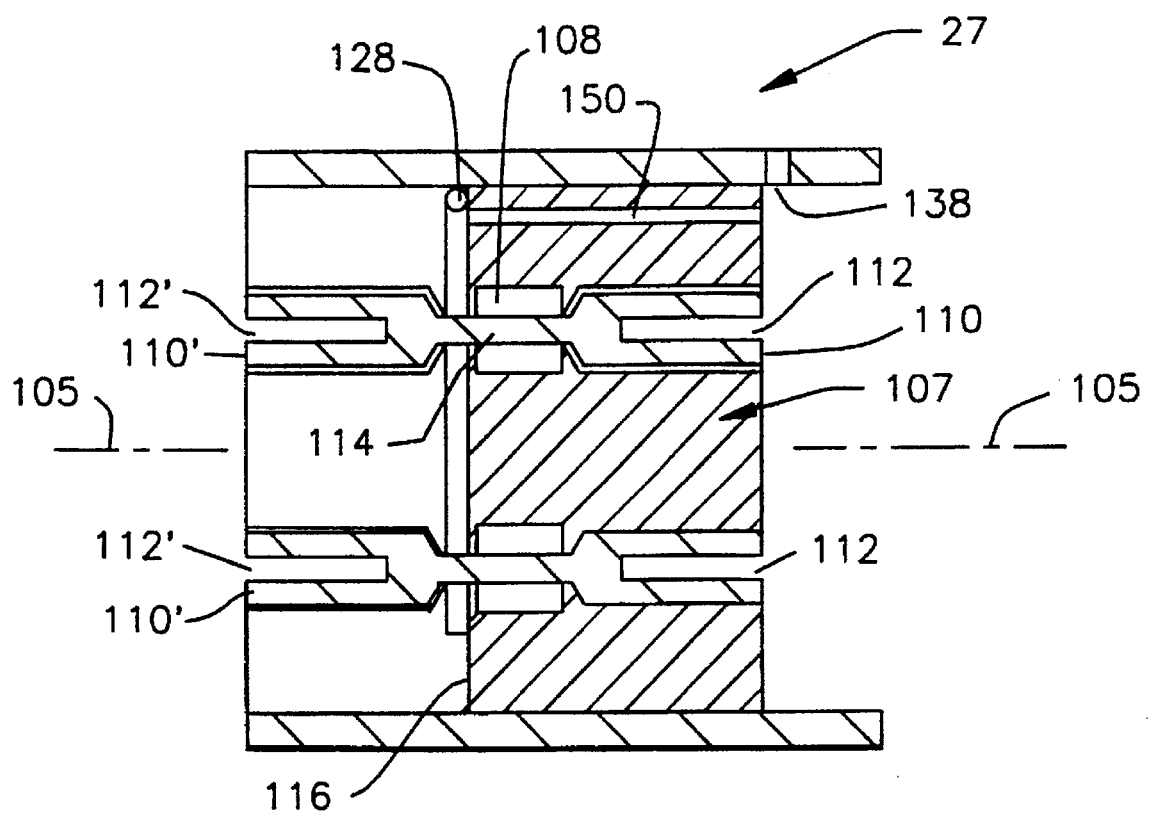
FIG. 6E is a cross sectional view of a modification of the female connector of FIGS. 6A, 6B and 6C.

FIG. 6E illustrates a female connector like that of FIG. 6A in which a different means is provided for attaching a wire 82 that conveys rotary motion between male and female connectors to the member 106. Instead of flattening the prong 114 to half thickness, a tube 110' like the tube 110 of FIG. 6A is formed at the end of the member 106 that has a cavity 112' like the cavity 112 of FIG. 6A so that the wire 82 can be inserted in it.

Figure 7:
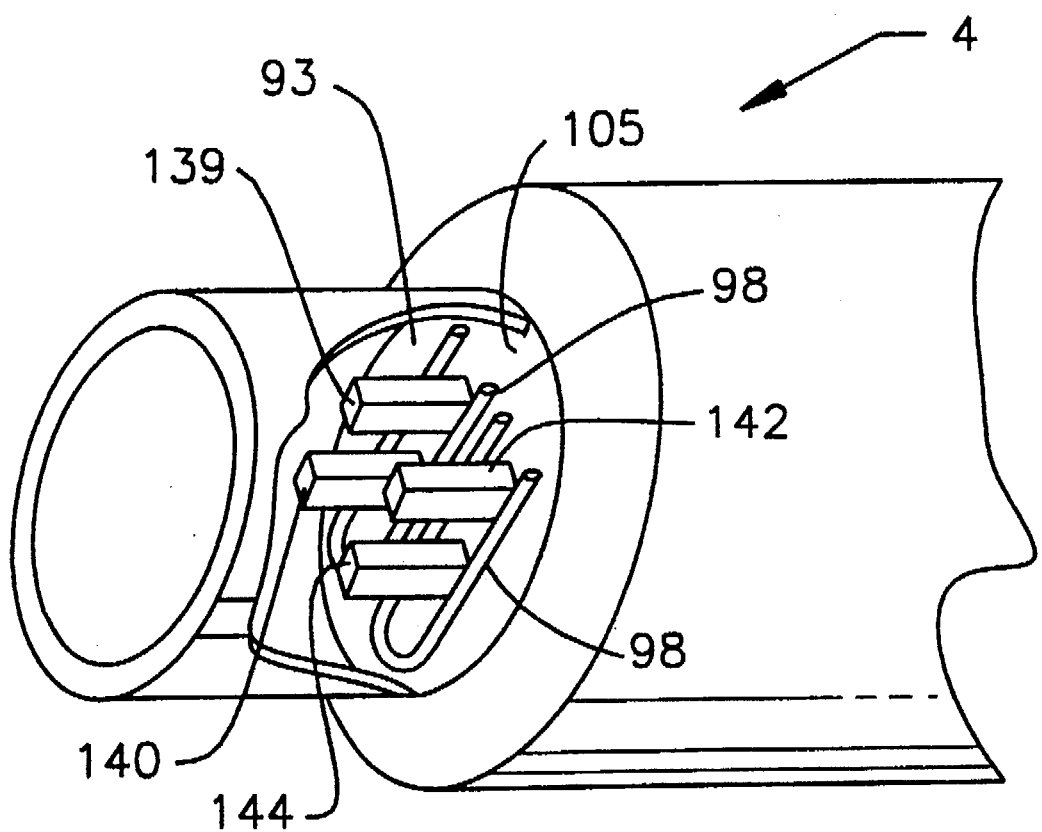
FIG. 7 is an isometric view of the exterior of a male connector.

FIG. 7 is an isometric partially cut-a-way view of a male connector like that of FIGS. 5A and 5B but having four rectangular male prongs 139, 140, 142, and 144 that are like the rectangular prong 92 of FIG. 5A that are to be inserted into similarly oriented cavities of a female connector, such as the cavities 112 of FIGS. 6A and 6C. Springs 98 like the spring 98 of FIG. 5A keep the ends 139, 140 and 142, 144, respectively, aligned when torque is not applied to them. Instead of being mounted on the wall 99 of the potting compound as in FIG. 5A, the springs 98 are mounted on the wall 93. One of the springs 98 straddles the prongs 139 and 140, and the other straddles the prongs 142 and 144.

When the male and female connectors are on opposite ends of joints of this invention, the rotary motion can be transmitted between the connectors by inserting one end of the wire 82 into the cavity 112 of a male connector of FIG. 5A, and the other end of the wire 82 into the cavity 112' of the female connector of FIG. 6E. Thus the wires are easily installed or removed. Alternatively, the wires 82 could be permanently connected to the members 88 and 106 so that the cavity 112 of FIG. 5A and the cavity 112' of FIG. 6E would not be necessary.

Conductors for carrying signals indicative of the rotational position of a joint are coupled through the male connector 4 and the female connector 27 in a similar way. In the male connector of FIG. 5A, a conductive tube 150 is retained within the potting compound 89 so as to be parallel to the axis 87 of the housing 86. The tube 150 is such as to provide a slide fit for a prong 152 at one end and such as to receive a connecting wire 153 at the other. The prong 152 is attached to the tube 150 in any suitable way such as soldering. The tube 150 extends from the wall 93, to the wall 99. The prong 152 of a male connector 4 can be inserted into the tube 150 of a female connector 27. In the female connector 27 of FIG. 6A and 6E, no prong 152 is required. The prong 152 of a male connector 4 can be inserted into the tube 150 of a female connector 27.

Two Axis Joint

Figure 8:
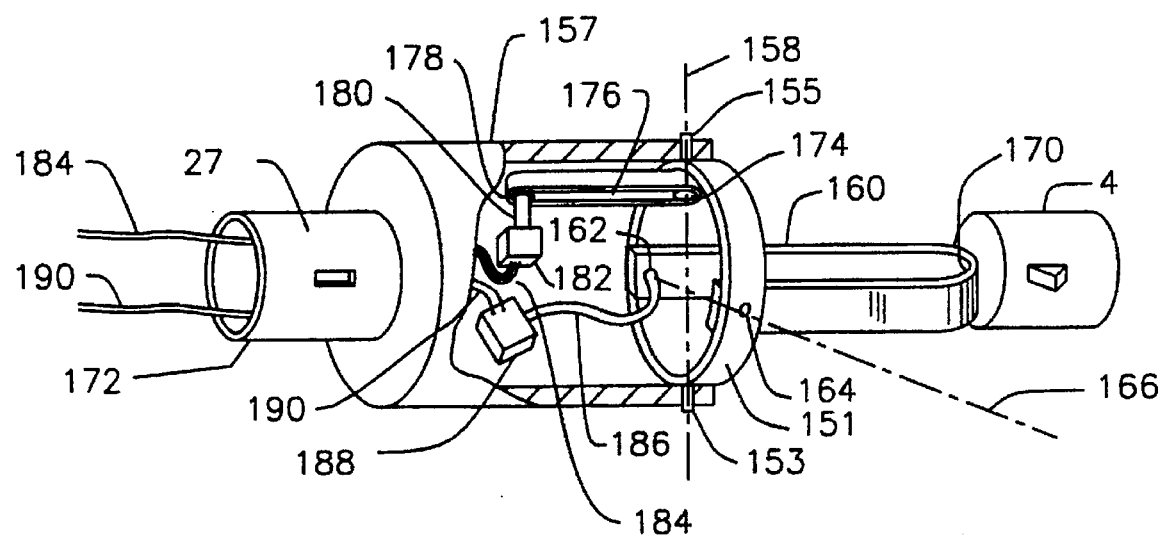
FIG. 8 is an isometric view of a two axis joint using a ring and a half-ring that rotate about respectively perpendicular axes.

In the two axis joint of FIG. 8, a ring 151 is coupled to diametrically opposed points 153 and 155 at one end of a hollow cylinder 157 so as to be able to pivot about an axis 158. A half ring 160 has its ends coupled to diametrically opposed points 162 and 164 on the ring 150 so as to be able to pivot about an axis 166 that is in the same plane as and at a right angle with the axis 158. A male connector 4 is firmly fastened to the mid point 170 of the half ring 160, and a female connector 27 is attached to the other end of the cylinder 157.

Providing a signal indicative of the angular position of the ring 151 about the axis 158 is accomplished in this particular embodiment by attaching a pulley 174 to the ring 151 so as to pivot therewith about the axis 158 and running a belt 176 around the pulley 174 and a pulley 178 that is mounted for rotation on the inside of the cylinder 157. As shown, the pulley 178 is mounted on an axle 180 extending from a device 182 that is attached to the cylinder 157. The device 182 operates to produce an electrical signal on conductors 184 indicative of the angular position of the axle 180 which in turn is indicative of the angular position of the ring 151.

Providing a signal indicative of the angular position of the half ring 160 about the axis 166 is accomplished in this particular embodiment by attaching one end of the central wire, not shown, of a rotation transmitting cable 186 so as to rotate with the half ring 160 about the axis 166 and the other end to a device 188 that is mounted on the inside of the cylinder 157. The device 188 operates to produce an electrical signal on conductors 190 indicative of the angular position of the wire and hence of the half ring 160.

The means for providing an electrical signal indicative of the rotation of the ring 151 about the axis 158 could be used for providing an electrical signal indicative of the rotation of the half ring 160 about the axis 166 and vice versa. The conductors 184 and 190 can be passed through either of the connectors 4 or 27, but are shown as passing through the female connector 27.

Figure 9A:
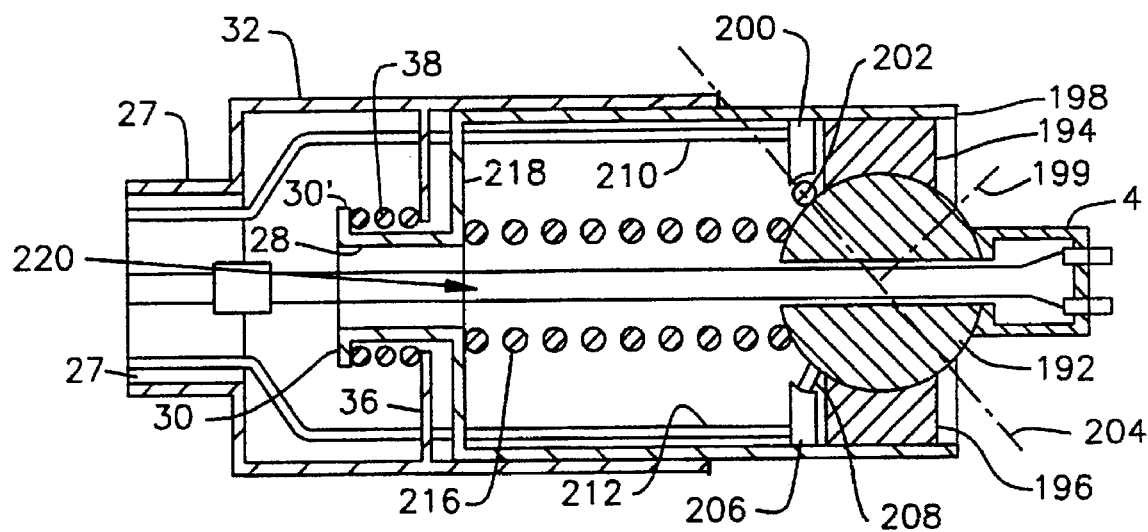
FIGS. 9A and 9B illustrate the monitoring means of a two axis joint in which a sphere is mounted so as to rotate about any axis.

Another two axis joint is illustrated in FIG. 9A wherein a sphere 192 is shown as being captured for rotation about any axis between spherically shaped ends of diametrically opposed inwardly extending projections 194 and 196 attached to an open end of a cylinder 198. Alternatively circular races of ball bearings could be mounted at the inner ends of the projections 194 and 196. Rotation of the sphere 192 about an axis 199 is detected by an electrical encoder 200 having a wheel 202 in contact with the sphere 192, and rotation about an axis 204 that is perpendicular to the axis 199 is detected by an electrical encoder 206 having a wheel 208 in contact with the sphere 192. If the female connector 27 is coupled to the cylinder 198 in a manner similar to the way it was coupled to the cylinder 22 in FIG. 1, conductors 210 and 212 from the encoders 200 and 206 are respectively passed through the bottom 218 of the cylinder 198, the flange 36 and the connector 27. Maintaining the axial alignment of the cylinders 32 and 198 is accomplished differently than the alignment of the cylinders 32 and 22 in FIG. 1 by extending the cylinder 32 along and in contact with the outside of the cylinder 198 instead of making the flange 30' large enough to contact the cylinder 32 as the flange 30 did in FIG. 1.

In order to return the sphere 192 to the position shown after torques have been released from it, one end of a coiled compression spring 216 is secured to the sphere 192 opposite the male connector 4 and coaxial with it. The other end of the spring 216 is secured to the annular bottom 218 of the cylinder 198 so that the spring in its untensioned state is coaxial with the cylinder 198 and the aperture 219 in the annular bottom 218.

Figure 9B:
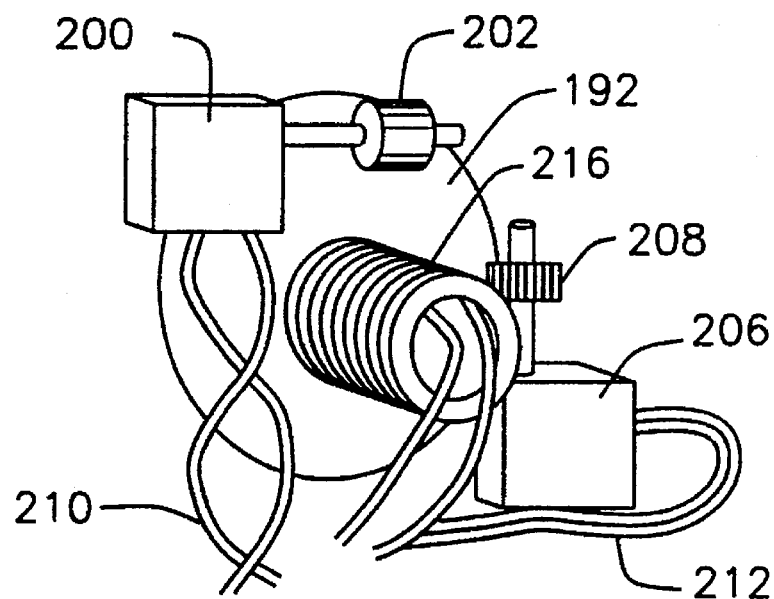

FIG. 9B is a view from the side of the sphere 192 showing the location of the encoders 200 and 206 and their respective wheels 202 and 208.

Figure 10:
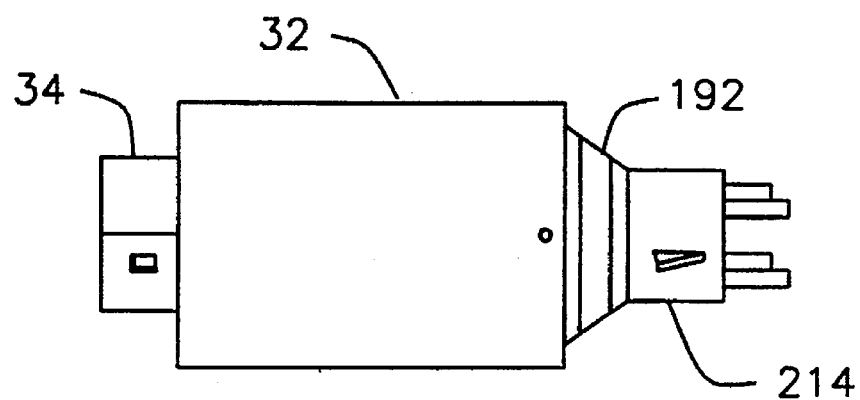
FIG. 10 is an external view of the two axis joint of FIGS. 9A and 9B.

FIG. 10 is an external side elevational view of the two axis joint of FIG. 9A.

Figure 11A:
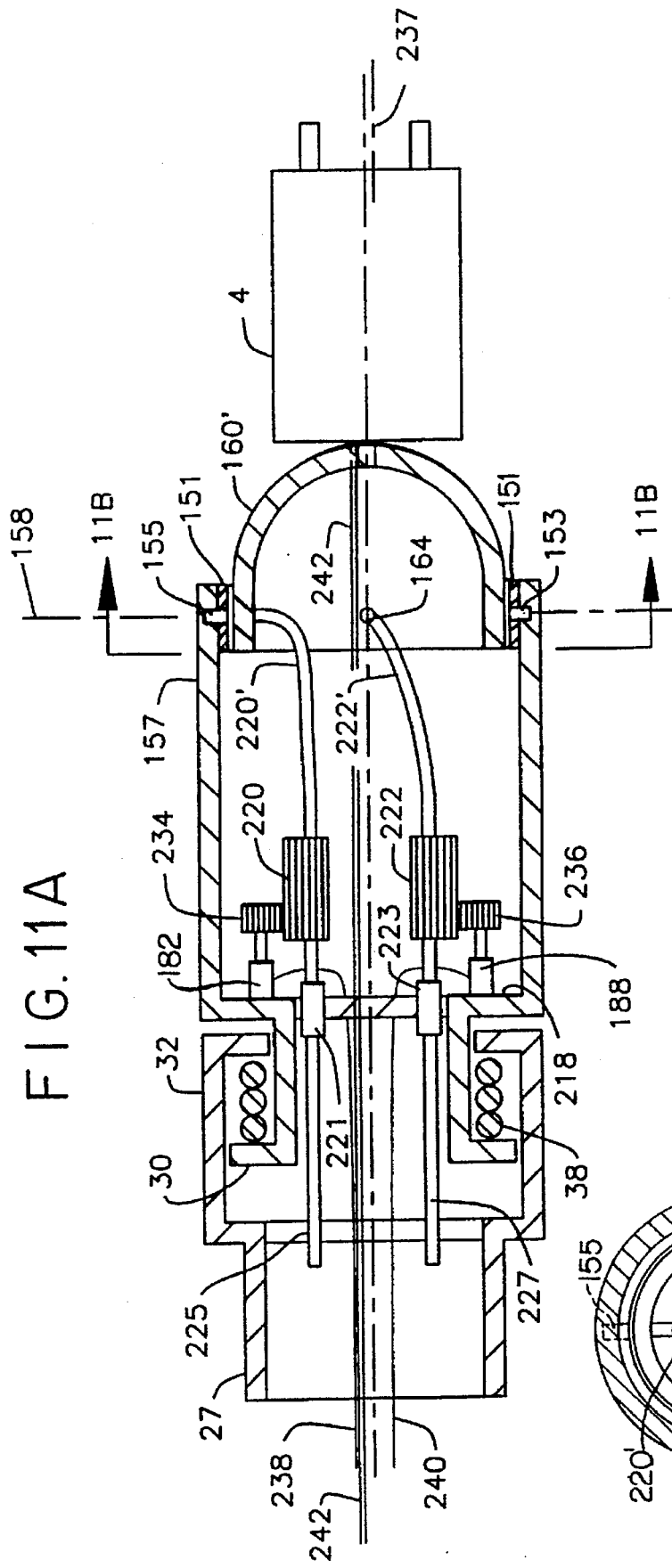
FIGS. 11A and 11B are sectional views of a two axis joint in which the positions of a ring and a half ring are controlled and monitored.
Figure 11B:
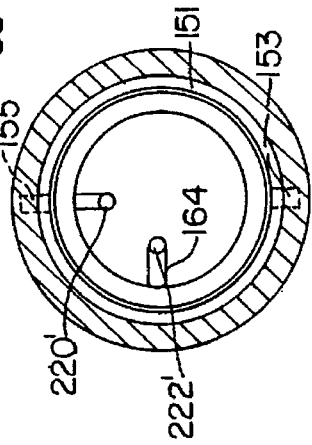

A side cross sectional view of FIG. 11A and a section 11B, 11B thereof illustrate a way of controlling and monitoring the positions of a two axis device similar to that of FIG. 8. Instead of the female connector 27 being firmly attached to a cylinder 157 as in FIG. 8, the connector 27 is coupled as in FIG. 1 so as to provide for elastic separation of the connectors 4 and 2T. Another difference is that the half ring 160 is replaced by a half sphere 160'.

A further difference is the way in which the rotation of the half sphere 160' and the full ring 151 about their respective axes is conveyed to the encoders 182 and 188 that are mounted in this embodiment of the invention on the bottom 218 of the cylinder 157. Gears 220 and 222 are respectively mounted so as to rotate with rotation transmission wires 220' and 222' respectively that pass from the female connector 27 to the respective points 155 and 164 of the ring 151 and the half sphere 160' respectively. The rectangular ends of the wires 220' and 222' and the rectangular ends of rotation transmission wires 225 and 227 are inserted in opposite ends of similarly shaped passageways, not shown, in bearings 221 and 223 in the bottom 218 of the cylinder 157 thus allowing relative longitudinal motion between the wires 225 and 220' and between the wires 227 and 222'. When the gears 220 and 222 turn with the wires 220' and 222', a gear 234 that is meshed with the gear 220 and a gear 236 that is meshed with the gear 222 activate the respective encoders 182 and 188 so as to produce electrical signals on conductors 238 and 240. A rotation transmission wire 242 passes between the male connector 4 and the female connector 27. Whereas it might appear that significant errors are introduced by virtue of the fact that the angular positions of the joints are derived from the wires causing their rotation, note that the gears 220 and 222 that drive the encoder 182 and the gears 222 and 236 that drive the encoder 188 are close to the axes 158 and 164.

Figure 12B:
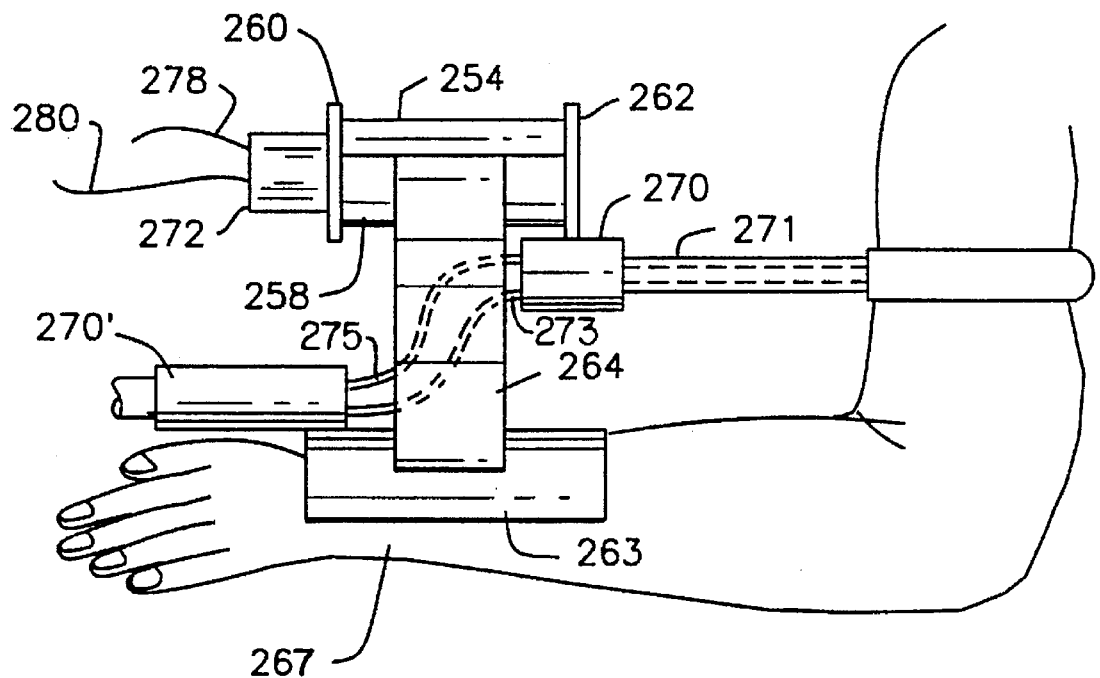
Figure 12A:
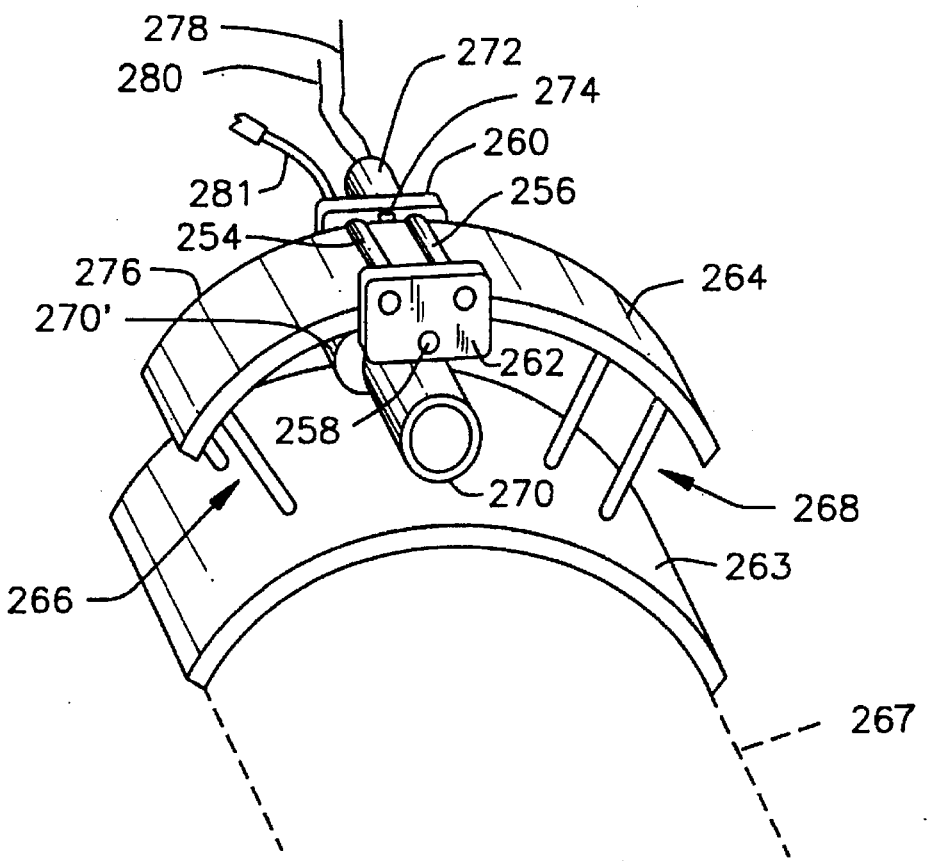

FIGS. 12A and 12B illustrate means for controlling and monitoring the rotation of a wrist about an axis extending along the forearm 267. As best viewed in FIG. 12A, parallel rollers 254, 256 and 258 are mounted for rotation about their respective axes between two plates 260 and 262. Passing between the roller 258 and the rollers 254 and 256 is a curved band 264 having posts 266 and 268 at the ends that are respectively attached to a curved member 263 attached to forearm 267. A cylinder 270 is attached to the plate 262 so that its axis is parallel to the axis of curvature of the band 264. The cylinder 270 is rigidly connected via a brace 271 to something such as the upper arm having a position that is not disturbed by rotation of the wrist so that the band 264 moves through the rollers 254, 256 and 258 when wrist turns. The cylinder 270 can be constructed as a male connector 4, and a cylinder 270' that is mounted on the member 263 can serve as a female connector. Rotation transmission cables and electrical conductors such as indicated at 273 and 275 can be connected between the cylinders 270 and 270'.

An electrical encoder 272 is mounted on the plate 260 in line with an aperture 274 so that it can respond to markings, not shown, on the side 276 of the band 264 and provide electrical signals on leads 278 and 280 indicative of the relative rotational positions of the band 264 with respect to the rollers 254, 256 and 258 and theretofore the angular position of the wrist with respect to the cylinder 270. Alternatively, a device as shown in FIG. 4 can be placed in line with any of the rollers 254, 256, 258 so as to provide signals indicative of the angular rotation of the wrist. As shown in FIG. 12A, a wire 281 of a rotation transmitting cable is axially connected to one of the rollers, e.g. the roller 254, so as to make it possible to rotate the band 264 and a wrist attached to it.

FIGS. 13A and 13B illustrate apparatus for controlling and monitoring the translational distance that a first point that may be coupled to a part of a body by a number of joints moves with respect to a second point that may be coupled to a reference point by a number of joints. A carriage 282 that slides along a bar 284 is provided with an optical encoder 286 that produces electrical signals in response to marks 288 on a side of the bar 82 indicating its position along the bar. A male connector 290 on the carriage 282 may be directly connected to a reference point 292, herein shown by way of example as a point on a wall 294, or it may be coupled thereto via a number of devices schematically represented at 296 permitting planar angle rotation as well as axial rotation. For reasons to be explained in connection with FIG. 15, another connector 298 is on the other side of the carriage 282.

One end of the bar 282 is attached to a connector 300 that may be directly attached to a part of a body such as a forearm 301 or it may be coupled to the forearm 301 via a number of devices schematically represented at 302 permitting planar angle rotation as well as axial rotation. Since the dimensions of the devices and the planar and axial angles as well as the location of the carriage 282 along the bar 282 are known, the movement of the forearm 301 with respect to the reference point 292 can be calculated.

FIG. 13B is a section 13B, 13B of FIG. 13A showing only those components that move the carriage 282 along the bar 284. A center conductor 304 of a rotation transmission cable 306 that passes through the connector 298 is attached to the center of a gear 308 that meshes with teeth 310 on a side of the bar 284. Thus, as the wire 304 turns about its axis, the gear 308 turns so as to move the carriage along the bar 284. In order that the carriage 282 move easily, suitable bearings 312 and 314 are provided at its opposite ends. In order to return the carriage 282 to a given position when all forces are removed, a pulley 311 is mounted so as to rotate with the wire 304 and a spring 313 is connected between the bearing 314 and one end of a string 315 that is wrapped around the pulley 311. Alternatively, the carriage 282 can be returned to an initial position by a mechanism such as shown in FIG. 2A.

Figure 14A:
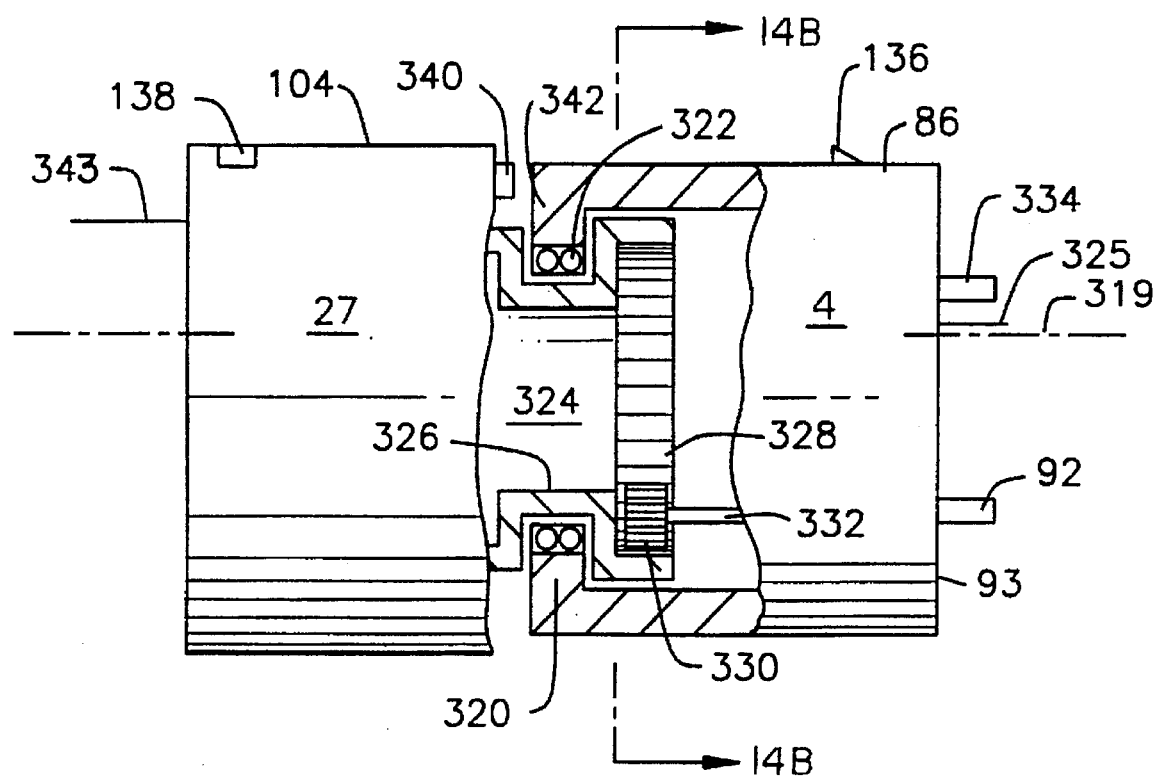
FIGS. 14A and 14B are sectional views of an axial rotation joint.
Figure 14B:
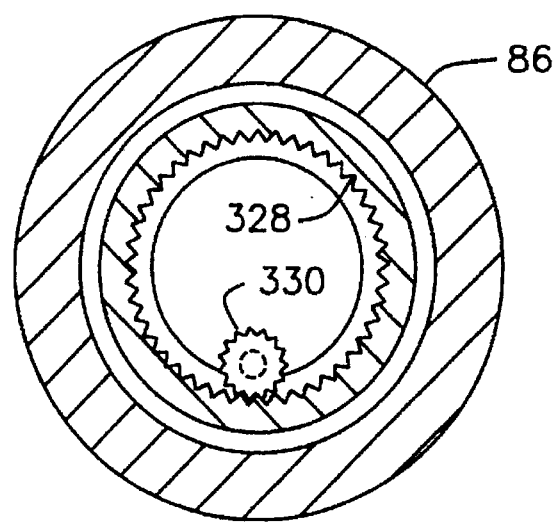

Mention has been made of an axial rotation joint that permits relative rotation of members about a common axis. An embodiment of such a joint that is depicted in FIG. 14A comprises a male connector 4 such as shown in FIG. 5A, and a female connector 27 such as shown in FIGS. 6A or 6E coupled together along a common axis 319. To simplify the drawing, the internal structure of the connectors 4 and 27 is omitted, but the structure for coupling them together is shown in cross section.

In this particular embodiment, the male connector 4 is modified by extending its housing 86 toward the female connector 27 and forming an inwardly extending annular ridge 320 thereon. An annular bearing 322 is attached to the inside of the ridge 320. One end of an annular hub 324 is attached to the housing 104 of the female connector 27, and its central section 326 is shaped to fit around both sides the annular ridge 320 and the annular bearing 322 in such manner that it is free to revolve with the female connector 27. An annular gear 328 is formed on the inside of the other end of the hub 324.

A male prong 92 that is mounted for axial revolution as shown in FIG. 5A, and a gear 330 that meshes with the annular gear 328 are coupled so as to rotate together by a shaft 332 that is inserted into the cavity 96 in a member 88, not shown. Because of the meshing of the gears 328 and 330, the prong 92 and the female connector 27 turn together. The rotation of any other prong such as 334 is coupled to turn a member 106 in the female connector 27 as explained in connection with FIGS. 5A, 6A and 6E. The interconnection wires as well as any conductors pass through the center of the annular hub 324.

Electrical signals indicative of the relative rotational positions of the male connector 4 and the female connector 27 are attained by an optical encoder 340 that is mounted on the housing 104 of the female connector 27 so as to observe markings 342, not shown, on the annular ridge 342 of the male connector 4. The signals are conveyed by a conductor 343 that is shown as passing through the female connector 27, but it could pass in the other direction through the male connector 4. Although not shown, rotation transmission cables and conductors of rotational position signals can pass through the connectors 4 and 27 and the hub 324.

Figure 15:
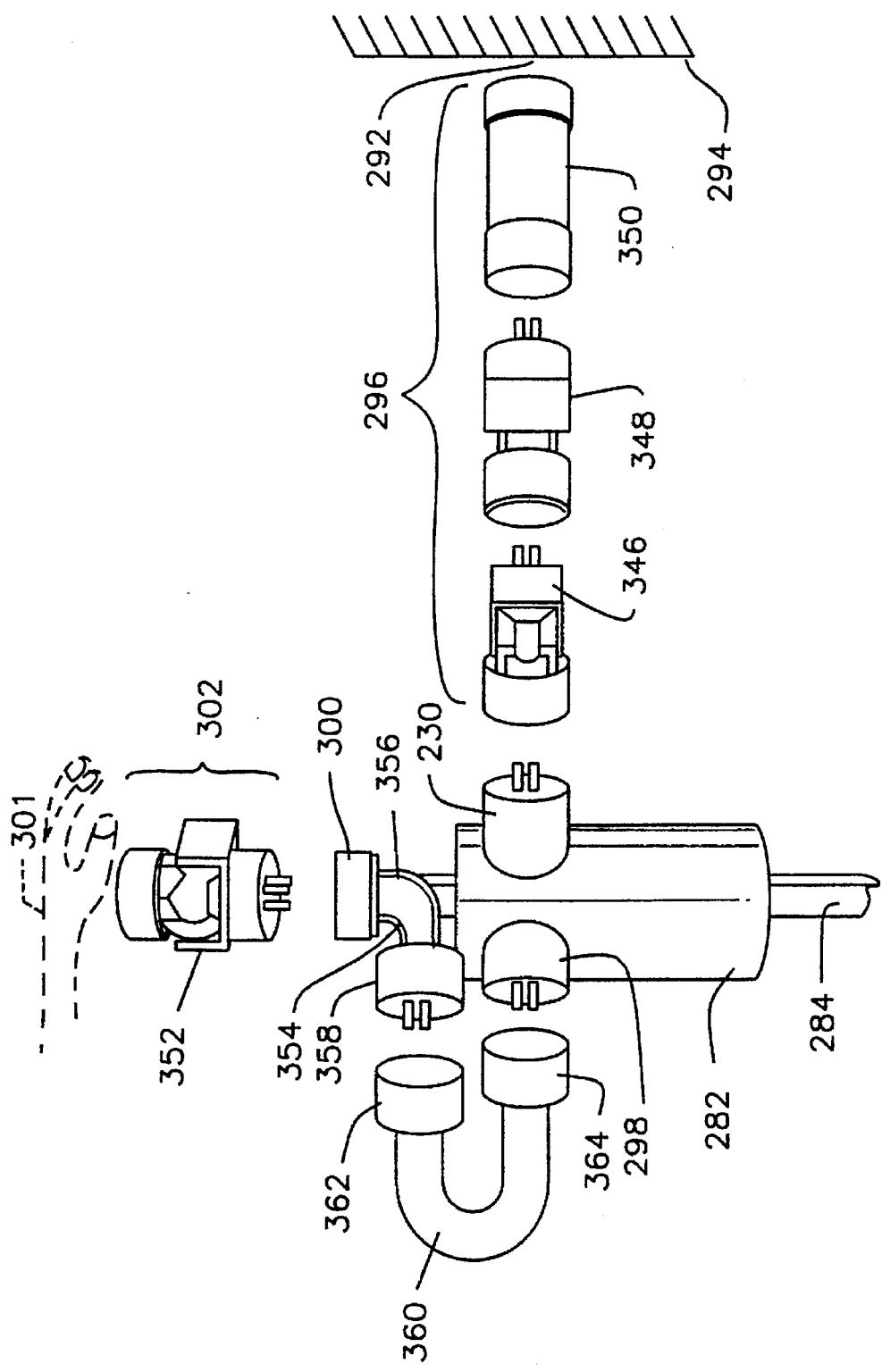
FIG. 15 illustrates an assembly of the various joints of the invention for controlling and monitoring the position of a hand with respect to a wall.

FIG. 15 illustrates one form of apparatus for using the linear motion translating device of FIGS. 13A and 13B in which the devices 296 that couple the device to a reference point 292 on a wall 294 comprise a single axis joint 346 that bends in and out of the plane of the paper, another single axis joint 348 that bends in the plane of the paper and an axial rotation joint 350 connected in the order named between the connector 230 and the reference point 292 on the wall 294. In this illustration, the device 302 that is coupled to a firearm 301 includes only a single axis joint 352.

Cables 354 and 356 from the female connector 300 are coupled to a male connector 358. A flexible tube 360 contains conductors and rotation transmission cables, not shown, that are connected between a female connector 362 that is to be connected to the male connector 358 and a female connector 364 that is to be connected to the male connector 298.

Since all the devices can be operated by twisting a wire of a rotation transmitting cable and monitored either electrically or mechanically, and since all devices permit cables and conductors to pass through them, a wide range of operating systems is available in FIG. 15. By way of example, the cables and conductors for a hand at the end of the forearm 301 shown in contact with the one axis joint 352 could be run to a controller, and all the cables and conductors for monitoring and operating the joints indicated at 302 and 296 as well as the carriage 282 could pass from the controller into the joints 252. One of these cables would be the cable 306 of FIG. 13B. Alternatively, all cables and conductors could be connected via the axial rotation joint 350. In fact, the conductors and cables for each joint could be connected directly to the controller in a manner to be described. Thus, one of the advantages of the invention is the great flexibility in connections for control and monitoring of the joints.

Figure 16:
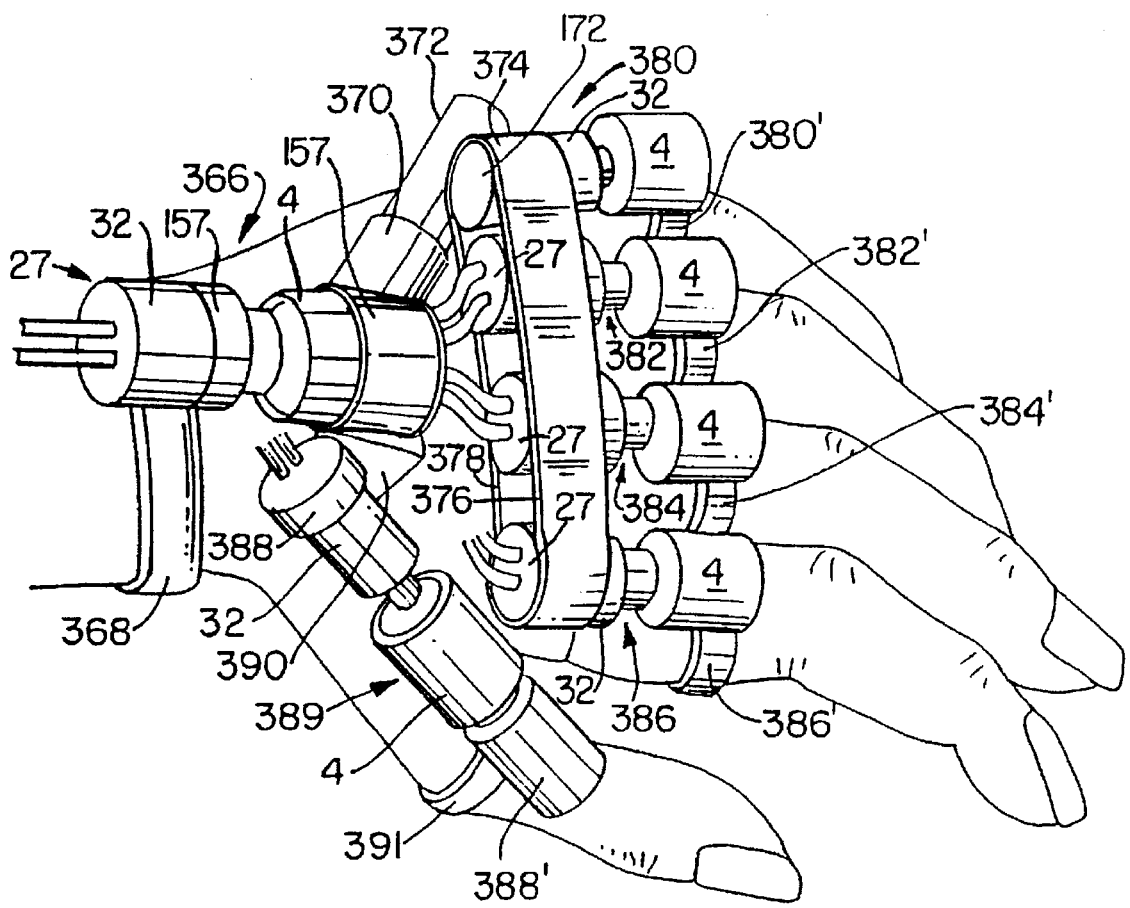
FIG. 16 illustrates an assembly of joints of this invention on a hand for controlling and monitoring its various parts.

FIG. 16 shows how joints of this invention may be attached to a hand. In this particular embodiment, a cylinder 32 of a two axis joint 366 that is like the joint of FIG. 11A is affixed to a wrist band 368, and the male connector 4 of the joint is connected via a cylinder 159 which fits over the male connector 4 and adjustable telescoping tubes 370 and 372 to a substantially rigid brace 374 that extends across the top of the hand. After the tubes 370 and 372 are adjusted for the particular hand involved, they are locked in position by means not shown so that the cylinder 157 of the two axis joint 366, the telescopic tubes 370, 372 and the brace 374 form a rigid structure. The brace 374 is comprised of spaced parallel bars 376 and 378 that are joined at their ends and are secured to respectively opposite sides of cylinders 32 of two axis joints 380, 382, 384 and 386 like that of FIG. 11A. The corresponding male connectors 4 of the two axis joints 380, 382, 384, and 386 are respectively attached to the part of each finger between the first and second knuckles by rings or clamps 380', 382', 384' and 386'.

The rotation of the main joint of a thumb is monitored or controlled by affixing a cylinder 32 of a two axis joint 389, such as shown in FIG. 11A, to the cylinder 159 via a cylinder 388 and a bracket 390, attaching an extension 388' to the other side at male connector 4, and clamping the extension 388' to the part of the thumb between the main joint and the knuckle of the thumb with a clamp 391.

The two axis joint 366 could be reversed so that the cylinder 159 would be attached to any of the cylinders 27, 32, 157 or 4. The joints 380, 387, 384 and 386 could be attached to the brace 374 by connecting the bars 376 and 378 to any of the cylinders 27, 32 or 157.

From this description, it will be understood that the rotation of the joint 366 follows the rotation of the wrist with respect to the forearm. Any rotation of the wrist about an axis along the forearm is uniquely monitored or controlled by a device not shown of FIGS. 12A and 12B, and rotation of the fingers about their respective first knuckles is monitored or controlled by the two axis finger joints 380, 382, 384 and 386, respectively. The rotation of the thumb is monitored and controlled by the joint 389. In order to simplify the drawings, the various cables and conductors associated with the operation of the joints have not been shown, but for example, the cables and conductors for each of the two axis finger joints 380, 382; 384, and 386; could be passed through the joint 366 as shown in FIG. 11A. Alternatively, the cables and conductors associated with the wrist joint 366 as well as the cables and conductors for the thumb joint 389 could be passed through any of the finger joints.

Figure 17:
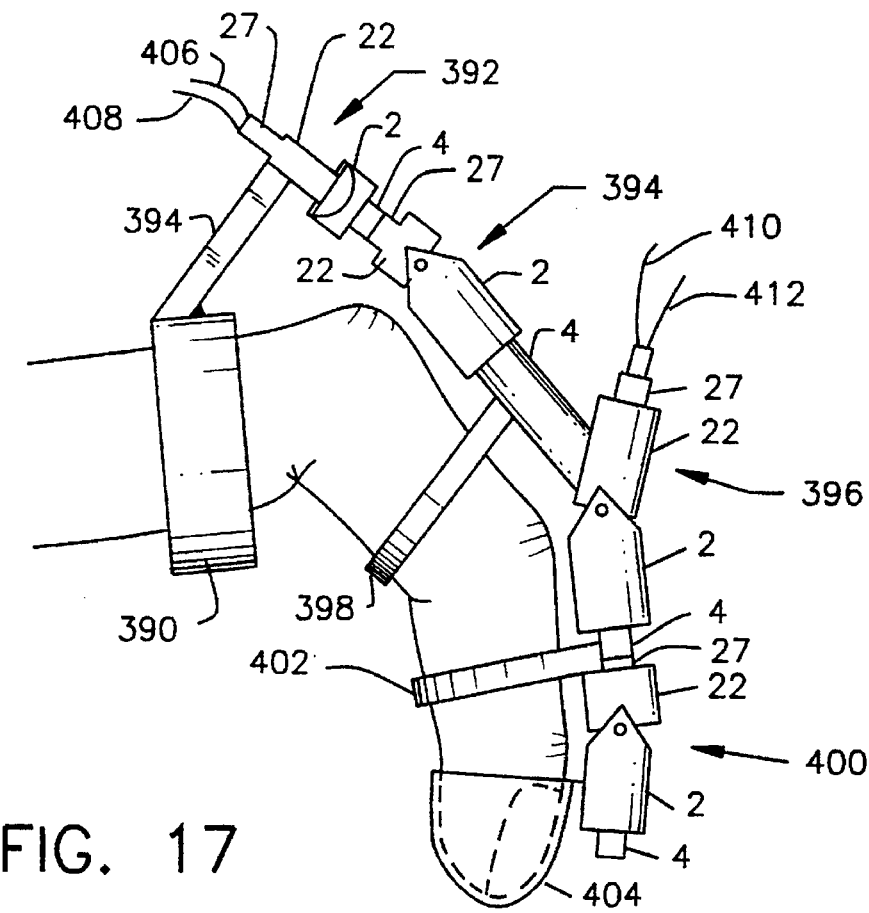
FIG. 17 illustrates the use of one axis joints of the invention for controlling and monitoring the joints of a finger.

FIG. 17 illustrates how a series of single axis joints such as shown in FIG. 1 may be used to control and/or monitor all sections of a finger. It may not be necessary, however, to use the elongation mechanism involving the spring 38, in which case the female connector 27 will be attached directly to the cylinder 22, and the cylinder 28 and the flange 30 will be eliminated. A palm brace 390 on the back of the hand curls around the edges of the palm and extends a little distance along it so as to make it easy to place in operating position. The female connector 27 and cylinder 22 of a single axis joint 392 that rotate in a plane perpendicular to the paper are firmly attached to the brace 390 by a bracket 394. A male connector 4 at the end of a cylinder 2 of the joint 392 is plugged into a female connector 27 of a single axis joint 394 that rotates in the plane of the paper. Thus the two single axis joints 392 and 384 are equivalent to a single two axis joint. A male connector 4 of the joint 394 is elongated and joined to a side of a cylinder 22 of a joint 396. A ring or clamp 398 attaches the male connector 4 to the portion of the finger between the first and second joints. The male connector 4 of the joint 396 is plugged into the female connector 27 of a single axis joint 400. A ring or clamp 402 attaches the cylinder 22 of the joint 400 to the portion of the finger between the second and third joints, and the cylinder 2 of the joint 400 is attached to a finger tip cap 404.

Whereas the cables and conductors related to the joints 396 and 400 could pass through the joints 394 and 392 so as to emerge from the female connector 27 of the joint 392 as indicted at 406 and 408, they can, instead, pass through the cylinder 22 of the joint 396 and emerge from its female connector 27 as indicated at 410 and 412. If desired, the male connector 4 of the joint 392 could be connected to the cylinder 22 of the joint 394 so as to connect these joints in the same way as the joints 394 and 396.

Figure 18:
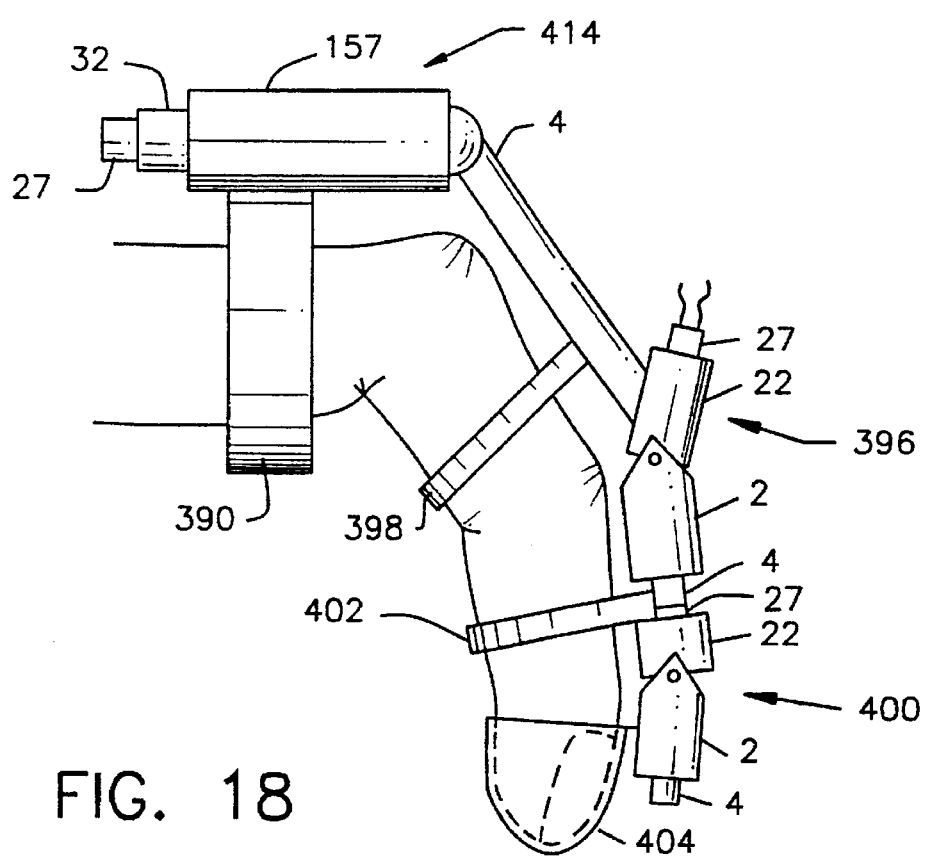
FIG. 18 illustrates the use of a two axis joint and several one axis joints for controlling and monitoring the joints of a finger.

FIG. 18 illustrates how the rotation of all joints of a finger can be monitored and controlled when using a two axis joint 414 like that shown in FIG. 11A, in place of the two single axis joints 392 and 394 of FIG. 17. A cylinder 157 of the joint 414 is attached to the palm brace 390, and its male connector 4 is extended and connected to a tube 22 of the joint 366 as in FIG. 17. From this point on, the device is the same as in FIG. 17, and corresponding parts are identified by the same numbers.

Figure 19:
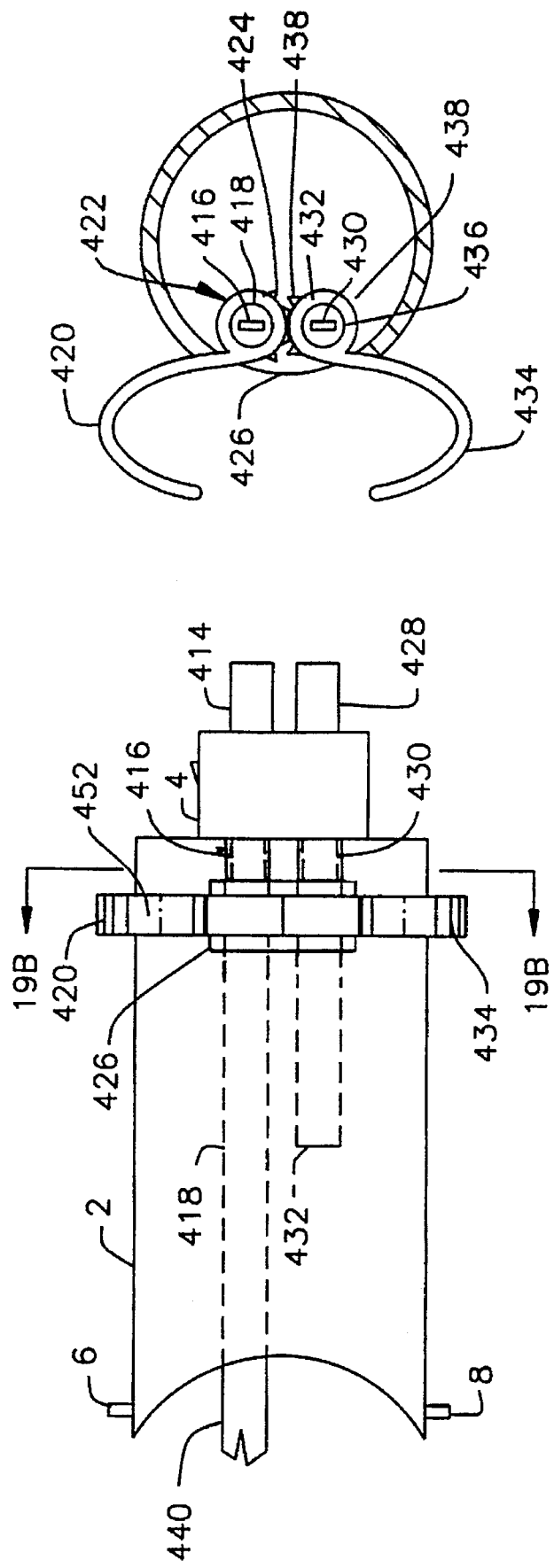
FIGS. 19A and 19B illustrate finger clamps that are remotely operated.

In order to make it easier to attach the clamps to the fingers, means are provided as shown in FIGS. 19A and 19B for providing clamps that can be opened when they are being placed on the fingers and closed when they are properly positioned. Parts corresponding to those of FIG. 1 are identified by the same numerals.

Rotation of a male prong 414 on one side of a male connector 4 causes a corresponding wire 416 on the other side of the connector 4 to rotate with it inside a housing 418. As better seen in FIG. 19B, which is a section 19B, 19B of FIG. 19A, a half clamp 420 shaped to fit one half of a finger has one end 422 wrapped around the housing 418 in such manner as to allow the end 422 to rotate about the housing 418. Gear teeth 424 are formed in the outside of the wrapped end 422 of the half clamp 420, and the clamp 420 extends through an aperture 426 in the cylinder 2.

Another male prong 428 on the said one side of the male connector 4 causes a wire 430 on the other side of the connector 4 and a housing 432 for the shaft 430 to rotate with it. Normally, the housing 432 would not rotate with the wire 430, but the two are attached in any suitable manner, as by adhesive, so as to rotate together. Alternatively, the housing 432 could be eliminated and the wire 430 replaced by a shaft. A half clamp 434 that is shaped to fit around half a finger has one end 436 wrapped tightly around the housing 432 and has gear teeth 438 on the end 436 that engage the teeth 424 on the end 422 of the half clamp 420. The half clamp 434 also protrudes through the aperture 426. Accordingly, it can be seen that rotation of the prong 428 causes the half clamps 420 and 434 to rotate in opposite directions.

Figure 20:
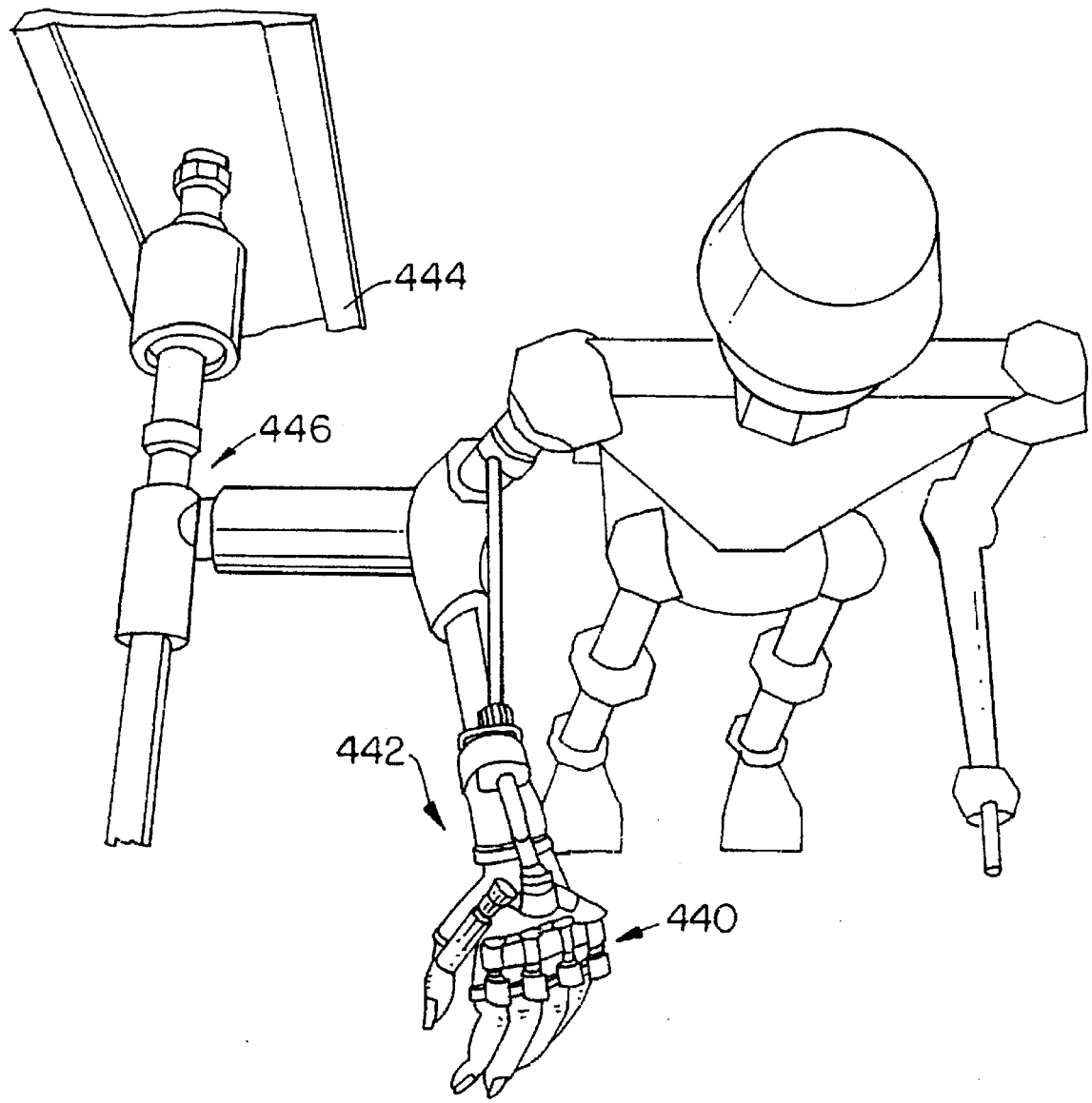
FIG. 20 illustrates the two systems of joints of this invention for controlling and monitoring the motion of an elbow, the rotation of a wrist about an axis passing through the elbow and the rotation of finger joints.

FIG. 20 illustrates another way of using the joints of this invention. Devices for monitoring and controlling finger and wrist motion as shown in FIG. 16 or FIG. 17 are generally indicated at 440. A device for monitoring and controlling the rotation of a wrist about an axis within the forearm as shown in FIGS. 12A and 12B is generally shown at 442, and devices for monitoring and controlling the transational motion of an elbow with respect to a wall 444 in a manner like that described in connection with FIG. 15 is generally shown at 446.

In the various embodiments of the invention three different ways for encoding the position of a joint are described, but it will be understood that encoding means shown in one embodiment can be used in others. By way of example, the encoding system of FIG. 11A wherein encoders are actuated very close to the points of application of rotation transmission wires controlling the position of a joint about respective axes could be used in the single axis joint of FIG. 1, and the use of a fibre optic cable in FIG. 1 could be used to indicate the angular position of each joint in FIG. 11A. Furthermore, the encoding means in FIG. 4 could be used to indicate rotation about any axis.

Although all of the joints have certain capabilities, all the structures for providing them are not shown in the drawings illustrating the respective joints as this would make them so complicated as to be confusing. These matters are clarified by the following comments.

Where the details of a male connector 4 or of a female connector 27 are not shown, it is understood that the male connector 4 will be as shown in FIGS. 5A and 5B and that the female connector 27 could be as shown in FIGS. 6A or 6E. In the claims, the word connector refers to a connector that can translate rotary motion of a wire on one side of it to a wire on the other and may as well transmit electrical signals if required. Generally, a male connector is shown on one end of a joint and a female connector is shown at the other, but they could be interchanged. Furthermore, if desired for some application, two male connectors or two female connectors could be used. This type of connector makes it possible to pass the rotation related to one joint through another.

It should be understood that the apparatus of FIG. 2A that resiliently urges the cylinders 2 and 22 into coaxial alignment could be used for aligning other members. For example, the apparatus of FIG. 21 could be used to orient the shaft 20 of FIG. 1, the shaft 60 of FIGS. 3A, 3B and 3C, the axle 180 and the cable 186 of FIG. 8, the wires 220' and 222' of FIG. 11A, any one of the rollers 254,256 and 258 of FIG. 12A, the center conductor 304 of FIG. 13B, and the shaft 332 or FIG. 14A.

The axial encoder of FIG. 4 can be used to derive an electrical signal indicating the angular position of any shaft about its axis.

The structure including the compression spring 38 of FIGS. 1, 9A and 11A that permits elastic elongation of a joint so as to make it easier to fit the joint into a system may also be used in the joints of FIGS. 3, 8, 10, 12 and 16.

Although various embodiments of the invention are shown and described herein, they are not meant to be limiting. Those of skill in the art may recognize certain modifications to the embodiments of the invention, which modifications are meant to be covered by the spirit and scope of the appended claims.

What is claimed is:

1. A joint comprising:

a first hollow housing having a first axis;

a second hollow housing having a second axis;

means for pivotally connecting diametrically opposed points on an end of said first hollow housing with respective diametrically opposed points on an end of said second hollow housing so that said housings pivot about a pivot axis;

a wire mounted for axial rotation within one of said first and second hollow housing; and means for changing the angle between the first and second axes of said first and second hollow housings in response to axial rotation of said wire.

2. The joint as set forth in claim 1, further comprising;

a male connector coupled to an outer end of one of said first and second cylinders;

said male connector being comprised of a third cylinder having an axis;

a wall within said third cylinder that is perpendicular to its axis and at a given distance from one end thereof;

means defining at least one passageway extending from said wall toward the other end of said third cylinder;

means defining an annular groove communicating with said passageway; and a U shaped spring mounted on said wall with its arm on opposite sides of said passageway.

3. The joint as set forth in claim 2, further comprising:

a female connector coupled to the outer end of the other of said first and second cylinders;

said female connector being comprise of a forth cylinder having an axis;

a wall within said fourth cylinder that is perpendicular to its axis and at a given distance from one end thereof;

means defining a passageway extending from said wall to the other end of said fourth cylinder;

means defining an annular groove communicating with said last mentioned passageway;

a female plug having a cylinder portion and a flange at one end, the flange engaging said last mentioned annular groove;

means defining an opening in the cylindrical portion of said member having a rectangular cross section; and a U shaped spring attached to said wall with its arms on either side of said last mentioned passageway.

4. A male connector comprising:

a housing having a first axis;

a longitudinal member having a prong with a cross section that is other than circular extending from one end and a tube extending from the other end and means defining a cavity in said tube having other than a circular cross section;

a wall in said housing that is transverse to said first axis;

means for mounting said longitudinal member for axial rotation within said housing and parallel to the first axis with its prong extending from one side of said wall and its tube exposed to the other side of said wall;

a U shape spring having parallel legs extending from a closed end; and means for affixing the closed end of said spring on said other side of said wall with its legs on opposite sides of said cavity.

5. A male connector comprising:

a housing having a first axis;

a longitudinal member having a second axis and comprised of a prong with a cross section other than circular at one end and a tube having a cavity therein extending from the other end, said cavity having a cross section other than circular;

a wall in said housing that is traverse to said first axis;

means for mounting said longitudinal member for rotation about said second axis with that second axis being parallel to said first axis of the housing, the prong extending on one side of said wall and said means for mounting preventing longitudinal movement of said longitudinal member;

a U shaped spring having parallel legs extending from a closed end; and means for affixing the closed end of said spring to said wall with its legs contacting opposite sides of said prong.

6. A female connector comprising:

a housing having a first axis;

a longitudinal member comprised of first and second tubular sections on either side of a section having an external rectangular cross section;

a wall transverse to said first axis of said housing;

means for mounting said member within said housing for rotation about said second axis with that second axis being parallel to the first axis of said housing and the rectangular section on one side of said wall;

means for preventing longitudinal movement for said longitudinal member;

a U shaped spring having parallel means for prevention longitudinal movement of said longitudinal member legs extending from a closed end; and means for affixing the closed end of said spring to one side of said wall with its legs contacting opposite sides of said rectangular section.

\* \* \* \* \*